(12) United States Patent
Longo et al.

(10) Patent No.: US 12,571,056 B2
(45) Date of Patent: Mar. 10, 2026

(54) METHOD AND KIT FOR THE IDENTIFICATION OF *Vaccinium myrtillus*

(71) Applicant: INDENA S.P.A., Milan (IT)

(72) Inventors: Valeria Longo, Milan (IT); Davide Berlanda, Milan (IT)

(73) Assignee: INDENA S.P.A., Milan (IT)

( * ) Notice: Subject to any disclaimer, the term of this patent is extended or adjusted under 35 U.S.C. 154(b) by 1160 days.

(21) Appl. No.: 17/604,301

(22) PCT Filed: Apr. 6, 2020

(86) PCT No.: PCT/EP2020/059807
§ 371 (c)(1),
(2) Date: Oct. 15, 2021

(87) PCT Pub. No.: WO2020/212190
PCT Pub. Date: Oct. 22, 2020

(65) Prior Publication Data
US 2022/0186326 A1 Jun. 16, 2022

(30) Foreign Application Priority Data
Apr. 16, 2019 (EP) .................................... 19169555

(51) Int. Cl.
*C12Q 1/6895* (2018.01)
*C12Q 1/686* (2018.01)

(52) U.S. Cl.
CPC .......... *C12Q 1/6895* (2013.01); *C12Q 1/686* (2013.01)

(58) Field of Classification Search
None
See application file for complete search history.

(56) References Cited

FOREIGN PATENT DOCUMENTS

| CN | 1372005 | A | 10/2002 |
|---|---|---|---|
| CN | 102146477 | A | 8/2011 |
| CN | 102222969 | A | 10/2011 |
| CN | 102732513 | A | 10/2012 |
| CN | 104673930 | A | 6/2015 |
| CN | 105063203 | A | 11/2015 |
| CN | 105603107 | A | 5/2016 |
| CN | 105624291 | A | 6/2016 |
| CN | 106119394 | A | 11/2016 |
| CN | 107142329 | A | 9/2017 |
| CN | 107653330 | A | 2/2018 |
| CN | 108642207 | | 10/2018 |
| EP | 1642976 | A1 | 4/2006 |
| EP | 2518145 | A1 | 10/2012 |
| ES | 2176066 | A1 | 11/2002 |
| JP | 2007-282626 | A | 11/2007 |
| WO | 2004101794 | A1 | 11/2004 |
| WO | 2006/020147 | A2 | 2/2006 |
| WO | 2011078093 | A1 | 6/2011 |

OTHER PUBLICATIONS

Parker et al., "Field-based species identification of closely-related plants using real-time nanopore sequencing," Scientific Reports, 2017, vol. 7, No. 1, 8 pages.
Janzen et al., CBOL Plant Working Group, "A DNA barcode for land plants," Proc Natl Acad Sci U S A, Aug. 4, 2009, vol. 106, No. 31, pp. 12794-12797.
Fazekas et al., "DNA barcoding methods for land plants," Methods and Protocols, Methods in Molecular Biology, 2012, vol. 858, pp. 223-252.
Laura Jaakola, et al., "Novel approaches based on DNA barcoding and high-resolution melting of amplicons for authenticity analyses of berry species", Food Chemistry, vol. 123, No. 2, Nov. 1, 2010, pp. 494-500 (7 pages).
Janne J. Koskimaki, et al., "Flavonoid biosynthesis and degradation play a role in early defence responses of bilberry (*Vaccinium myrtillus*) against biotic stress", European Journal of Plant Pathology, vol. 125, No. 4, Jul. 23, 2009, pp. 629-640 (12 pages).
Matteo Marieschi, et al., "Authentication of *Punica granatum* L.: Development of SCAR markers for the detection of 10 fruits potentially used in economically motivated adulteration", Food Chemistry, vol. 202, Feb. 2, 2016, pp. 438-444 (7 pages).
"Vaccinium Myrtillus internal transcribed spacer 1, 5.8S ribosomal RNA gene, and internal transcribed spacer 2, complete sequence", XP002793914, Jul. 11, 2002, 1 page.
International Search Report and Written Opinion of the ISA for PCT/EP2020/059807 dated May 27, 2020, 15 pages.
Office Action, issued in Japanese Patent Application No. 2021-560683 dated Mar. 5, 2024.

*Primary Examiner* — Katherine D Salmon
(74) *Attorney, Agent, or Firm* — NIXON & VANDERHYE

(57) ABSTRACT

Disclosed is a method for the identification of *Vaccinium myrtillus* in a botanical composition and a kit specifically designed for its implementation. The method is based on the detection, using PCR amplification, of nucleic acid fragments within a genomic region of *Vaccinium myrtillus*.

8 Claims, 23 Drawing Sheets

Specification includes a Sequence Listing.

Figure 2 a)

| Primer set | Sample | Cq | Cq Mean | Cq Std. Dev |
|------------|--------|------|---------|-------------|
| L2 | 1072/10/12 | 25.61 | 25.37 | 0.212 |
|    |            | 25.28 |         |       |
|    |            | 25.21 |         |       |
| S2 | 1072/10/12 | 26.17 | 25.89 | 0.247 |
|    |            | 25.70 |         |       |
|    |            | 25.80 |         |       |
| L  | 1072/10/12 | 24.88 | 25.11 | 0.203 |
|    |            | 25.20 |         |       |
|    |            | 25.25 |         |       |
| S  | 1072/10/12 | 25.97 | 26.15 | 0.166 |
|    |            | 26.19 |         |       |
|    |            | 26.29 |         |       | b)

Primer set L2

Primer set L

Primer set S2

Primer set S

○     Standard

▬     SYBR

E=106,1% R^2=0,975 Slope=-3,183 y-int=28,931

(a)

(b)

a)

b)

| | | | |
|---|---|---|---|
| 1. | 32549/H76_2 Large | 6. | 32549/H84_1 Small |
| 2. | 32549/H76_2 Small | 7. | 32549/H84_2 Large |
| 3. | 32549/H83_1 Large | 8. | 32549/H84_2 Small |
| 4. | 32549/H83_1 Small | 9. | Positive control Large |
| 5. | 32549/H84_1 Large | 10. | Positive control Small |

METHOD AND KIT FOR THE IDENTIFICATION OF *Vaccinium myrtillus*

This application is the U.S. national phase of International Application No. PCT/EP2020/059807 filed Apr. 6, 2020 which designated the U.S. and claims priority to EP patent application Ser. No. 19/169,555.0 filed Apr. 16, 2019, the entire contents of each of which are hereby incorporated by reference.

BACKGROUND OF THE INVENTION

Field of the Invention

The present invention provides a method for the identification of *Vaccinium myrtillus* in a botanical composition, which is based on the detection of specific genomic fragments using PCR amplification. The invention further provides a kit specifically designed for implementing the method of invention.

Description of the Related Art

Plant extracts are in widespread use in the medical, nutraceutical, cosmetic and food industry. One of the main issues encountered when dealing with plant extracts is that of determining not only their chemical composition, but also their botanical origin, in order to exclude the risk of counterfeit.

Genetic-based methods for determining the botanical origin of plant materials are known in the art (Parker, J., et al., *Field-based species identification of closely-related plants using real-time nanopore sequencing*. Sci Rep, 2017. 7(1): p. 8345; Group, C. P. W., *A DNA barcode for land plants*. Proc Natl Acad Sci USA, 2009. 106(31): p. 12794-7; Fazekas, A. J., et al., *DNA barcoding methods for land plants*. Methods Mol Biol, 2012. 858: p. 223). Such methods are based on the comparison of the DNA present in the plant material with known DNA sequences present in publicly available databases. For example, WO 2006/020147 (The Regents of the University of California) discloses a method for identifying individual biological genetic components present in a botanical mixture, said method being based on a combination of genomic-locus specific PCR, single strand conformation polymorphyspm (SSCP), and sequence analysis. The method is said to be able to provide information on the biologic components of the composition without requiring prior knowledge as to which botanicals may be present and to detect and identify unknown biologic components that may be present in the mixture.

Methods for the genetic identification of plants from botanical samples are also disclosed in CN102146477, CN106119394, CN1372005, CN107142329, CN107653330, CN105624291, CN105603107, ES2176066, CN104673930, CN102222969, CN102732513, CN105063203, JP2007282626. In some cases, the methods for the identification of botanical species are based on the detection, by PCR amplification, of specific sequences located within the nuclear ribosomal RNA-encoding locus containing the internal transcribed spacer (ITS) regions ITS-1 and/or ITS-2. In certain cases (CN1052429, CN105603107, ES2176066), the methods are aimed at identifying adulterations in commercialised products containing plant materials.

Jaakola L et al., Food Chemistry vol. 123, no. 2 (2010) pp. 494-500, discloses the identification of commercially important berry species by means of a combined approach of DNA barcoding and HRM (High Resolution Melting) analysis, using designed primer pairs which enable the species-specific identification of wild berries. *Vaccinium myrtillus* is identified through HRM analysis of an amplicon located in the ITS (Internal Transcribed Spacer) region obtained with primers ITSVm2f and ITSVm2r.

CN108642207 discloses the construction of an allelic map of the bilberry plant, and a method for the identification of blueberry varieties and related species using primer-specific PCR-amplification.

Marieschi M. et al, Food Chemistry vol. 202 (2016) pp. 438-444 discloses a method based on Sequence Characterized Amplified Regions (SCARs) to detect the presence of *V. myrtillus* and adulterating species useful for multiple batches analysis.

Koskima Ki J J et al., European Journal of Plant Pathology, Kluwer Academic Publishers—vol. 125 no. 4 (2009) pp. 629-640 discloses the relative expression of bilberry genes quantified by Real-Time PCR with SYBR-green as the fluorescent reporter.

When plant materials are processed and, in particular, when they are subjected to extraction procedures, the DNA degrades giving rise to fragments of variable size and amount according to the extraction method and which cannot be directly compared with known DNA sequences, thereby making it difficult, if not practically impossible, to apply to extracts the genomic identification methods that can be applied on the starting materials.

*Vaccinium myrtillus* extracts are largely used in pharmaceutical, cosmetic, nutraceutical and dietary products due to their known health-beneficial properties. The clinical benefits of *V. myrtillus* as both a dietary supplement and a therapeutic have been attributed to the presence of abundant amounts of flavonoids and anthocyanins. For extract manufacturers, it is important to guarantee that *V. myrtillus* extracts have the required specifications in terms of chemical components and the declared pure botanical origin. It would therefore be desirable to provide a method that allows to identify *V. myrtillus* in a botanical composition, e.g. in a plant extract, securing high levels of accuracy and species-specificity particularly when *V. myrtillus* is in admixture with closely related contaminant species.

SUMMARY OF THE INVENTION

These objectives are achieved by the present invention, which provides a method for the specific and accurate identification of *Vaccinium myrtillus* in a botanical composition through detection of a nucleic acid fragment which is contained in the residual DNA of *V. myrtillus* extracts.

Specifically, the method of invention comprises detecting, in a sample of botanical composition, a *V. myrtillus*-specific nucleic acid fragment located within the internal transcribed spacer 1, 5.8S ribosomal RNA gene and the internal transcribed spacer 2, wherein said nucleic acid fragment consists of either SEQ ID NO:1 or a sequence comprising SEQ ID NO:1 which is selected from the group of SEQ ID NOs:2, 3 and 4.

In a preferred embodiment, the primers used for PCR-amplification are selected from the following pairs:
(i) SEQ ID NO:5 and SEQ ID NO:6;
(ii) SEQ ID NO:7 and SEQ ID NO:8;
(iii) SEQ ID NO:9 and SEQ ID NO:10;
(iv) SEQ ID NO:11 and SEQ ID NO:12;

In a particularly preferred embodiment, the PCR is a real-time PCR (rtPCR) and the method of invention comprises the following steps:

(a) isolating nucleic acids from a sample of botanical composition;

(b) conducting a rt-PCR on the isolated nucleic acids, using:

a pair of primers selected from the group consisting of:
(i) SEQ ID NO:5 and SEQ ID NO:6;
(ii) SEQ ID NO:7 and SEQ ID NO:8;
(iii) SEQ ID NO:9 and SEQ ID NO:10;
(iv) SEQ ID NO:11 and SEQ ID NO:12;
and a probe annealing within the nucleic acid region amplified by the primers, said probe having sequence SEQ ID NO:13;

(c) determining the presence of the amplification product, whereby detection of the amplification product is indicative of the presence of *Vaccinium myrtillus* in the botanical composition.

According to the invention, the botanical composition is a mixture of plants or parts thereof, e.g. leaves, fruits, bark, roots, including plant extracts and particularly fruit extracts, which are intended for consumption or therapeutic use. In a preferred embodiment, the botanical composition is a product containing an extract of fruits of *Vaccinium myrtillus*, alone or in combination with related species such as *Empetrum nigrum, Sambucus nigra, Vaccinium oxycoccos, Vaccinium corymbosum* and *Vaccinium macrocarpon.*

The isolation of nucleic acids involves their separation and purification from other components of the plant mixture or extract and it can be conducted with conventional techniques using commercially available kits. In particular, the genomic DNA may be isolated using extraction-precipitation protocols, silica-membrane- or anion-exchange-based procedures.

Real-time PCR technology is known in the art and it combines the polymerase chain reaction chemistry with the use of fluorescent reporter molecules in order to monitor the production of amplification products during each cycle of the PCR reaction. The amplification of the target DNA is obtained by repeated cycles of denaturation followed by primer- and probe-annealing and by DNA polymerase-catalyzed primer extension. DNA amplification is monitored at each cycle of PCR by measuring a fluorescent signal which is produced for instance by non-specific fluorescent dyes that intercalate with double-stranded DNA or by sequence specific DNA probes consisting of oligonucleotides labelled with a fluorescent reporter which allows for detection after probe hybridization with its complementary DNA target. Suitable intercalating dyes include SYBR® (Green I, Green II, Gold), LCGreen®, SYTO-(9, 13, 16, 60, 62, 64, 82), BOBO-3, LCGreen®, POPO-3, BEBO, TO-PRO3, PicoGreen®, SYTOX Orange and similar commercially available fluorescent dyes (fluorophores).

The oligonucleotide probe is labeled with a fluorescent reporter (fluorophore) at one end and a quencher of fluorescence at the opposite end of the probe. The 5' exonuclease activity of the polymerase cleaves the probe releasing the reporter molecule resulting in an increase of the fluorescence intensity. Examples of fluorophores include 5- or 6-carboxyfluorescein (5- or 6-FAM), tetrachlorofluorescein (TET), hexachloro-6-carboxyfluorescein (HEX), 6-carboxy-4',5'-dichloro-2',7'-dimethoxyfluorescein succinimidyl ester (JOE), tetramethylrhodamine (TAMRA), 5-carboxytetramethylrhodamine (TAMRASE), carboxy-X-rhodamine (ROX), 4-(dimethylaminoazo)benzene-4-carboxylic acid (DABCYL). Examples of quenchers include those of the BHQ (Black Hole Quencher®) family, NFQ-MGB (non-fluorescent quencher and minor groove binder), QSY 7 or 21 carboxylic acid succinimidyl ester.

The parameters and conditions of the rtPCR, such as the temperature and the length of each cycle of denaturation and annealing, can be adjusted depending on the nucleic acid fragment to be amplified, on the set of primers used in the amplification and on other variables, as known to anyone skilled in the art. In a preferred embodiment of the invention, the nucleic acid fragments herein disclosed are amplified with primers (i) through (iv) applying the following conditions:

initial denaturation step at 95° C. for 180 sec 2-step cycles of 15 sec at 95° C. ($1^{st}$ step) and 15 sec at 62-68.5° C. ($2^{nd}$ step) repeated forty (40) to fifty (50) times.

The specific combinations of primers and probe according to the invention allows for the specific identification of *Vaccinium myrtillus* in botanical compositions containing closely related species such as *Empetrum nigrum, Sambucus nigra, Vaccinium oxycoccos, Vaccinium corymbosum* and *Vaccinium macrocarpon.* As reported in the experimental section, the use of a probe different from the *Vaccinium myrtillus*-specific probe SEQ ID NO:13 and likewise annealing with fragments SEQ ID NOs:1-4, abolishes the system ability to identify *Vaccinium myrtillus* in admixture with Empetrum using the same primers and rt-PCR conditions disclosed above. This denotes the specificity of the selected combination of primers, probe and the effectiveness of the rtPCR conditions according to the invention.

Another aspect of the invention regards a kit for the identification of *Vaccinium myrtillus* in a botanical composition. The kit of invention comprises at least one pair of primers selected from (i) through (iv) and the probe as above defined. In addition the kit may comprise, in separate containers, reagents needed for running the (rt)PCR, particularly the deoxynucleotides and the DNA polymerase, and reagents for isolating, purifying and optionally quantifying DNA. The kit may also contain DNA of *Vaccinium myrtillus* as positive control and nuclease-free water or buffer as negative control, as well as a leaflet with the instructions for performing the PCR assay.

In a preferred embodiment of invention the kit contains:

one tube or vial containing all reagents necessary to perform the analysis (DNA Polymerase, dNTPs, Buffer, Probe chemistry, Primers and Probe)

one tube or vial containing the positive control (DNA of *Vaccinium myrtillus*)

one tube or vial containing the negative control DNA (Nuclease-free water)

The kit can be used with all commercially available Real-time PCR System.

BRIEF DESCRIPTION OF THE DRAWINGS

FIG. 10: Alignment analysis of sequenced amplicons (top) and relative sequence identity matrix (bottom).

DESCRIPTION OF THE PREFERRED EMBODIMENTS

Experimental Section—General Procedures

Extraction of Genomic DNA (gDNA)

The DNA extraction was performed by using the NucleoSpin® plant II protocol as described by the supplier (Macherey nagel. Cat. 740770.250—July 2014/Rev. 09).

Purification of Residual DNA from the Dry Extract.

The first purification was done by using the kit NucleoSpin® plant II Maxi protocol as described by the supplier (Macherey nagel. Cat. 740770.250—July 2014/Rev. 09), with some modification reported below.

Weigh 3-5 g of dry extract in a 50 ml conical tube

Add 3 ml of distilled water

Add 9 ml of lysis buffer

Vortex for 30 sec

Transfer the sample to a NucleoSpin® Filter Maxi

Centrifuge 5 min at 4500× g, collect the clear flow-through and discard the NucleoSpin Filter Maxi Add 20 ml binding buffer Vortex for 30 sec.

Load sample on a NucleoSpin® Plant II Maxi Column

Centrifuge for 3 min at 4500× g and discard the flow-through.

Repeat the loading for all the resting sample

Add 4 ml wash buffer (PW1) to the NucleoSpin® Plant II Maxi Column

Centrifuge for 3 min at 4500× g and discard the flow-through.

Add 10 ml wash buffer (PW2) to the NucleoSpin® Plant II Maxi Column

Centrifuge for 3 min at 4500× g and discard the flow-through.

Add 2 ml wash buffer (PW2) to the NucleoSpin® Plant II Maxi Column

Centrifuge for 12 min at 4500× g and discard the flow-through.

Place the NucleoSpin® Plant II Maxi Column into a new collection tube (50 ml)

Pipette 1000 μl elution buffer (PE) (65° C.) onto the membrane.

Incubate the NucleoSpin® Plant II Maxi Column for 5 min at 65° C.

Centrifuge for 3 min at 4500× g to elute the DNA

The second purification was done by using the kit ReliaPrep™ DNA Clean-UP and Concentration System protocol as described by the supplier (Promega. Cat. A2893).

Quantification of DNA

The DNA was quantified through the NanoQuant Plate™ instrument. The quantification was performed by using the UV-method. The 260 nm absorbance was used to quantify the DNA as 1 OD at 260 nm correspond to 50 μg/μl of DNA. The 260 nm/280 nm absorbance ratio was determined for the assessment of DNA purity.

rt-PCR and Melt Curve Analysis

Figure 1:
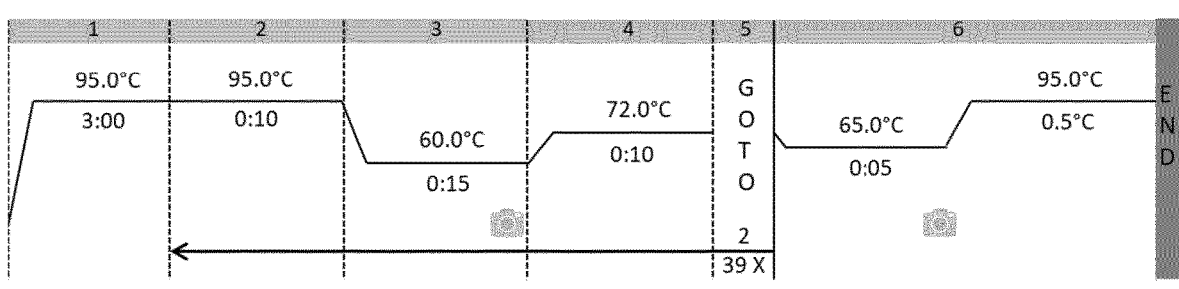
FIG. 1: rt-PCR amplification protocol.
Figure 1:
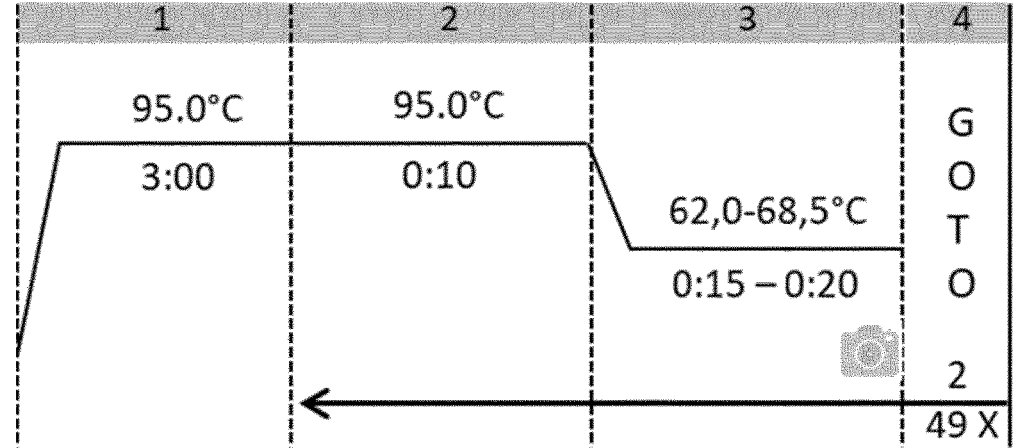

The rt-PCR amplification was performed by using the SYBR Green or probe based chemistry as described by the supplier (SsoAdvanced™ Universal SYBR® Green Supermix, BioRad Cat. N. 1725272; SsoAdvanced™ Universal Probes Supermix, BioRad Cat. N. 1725281), with 3-step based amplification protocol, as reported in FIG. 1.

Real-Time PCR

Prepare the mix as follos, final volume 20 μl:

| | |
|---|---|
| Probe Mastermix (BioRad or equivalent) 2X | 10 μl |
| Primer F 10 μM | 0.5 μl |
| Primer R 10 μM | 0.5 μl |
| Probe M-FAM 10 μM | 0.5 μl |
| DNA 0.5-30 ng/μl | 2 μl |
| Nuclease-free water | 6.5 μl |

Load the sample in a real-time instrument (BioRad or equivalent) and set the following method:

| | | |
|---|---|---|
| 95° C. | 180 sec | |
| 95° C. | 15 sec | 50 X |
| 62 C.-68.5° C. | 15 sec | |

Acquisition after the second step of cycling.

DNA Sequencing

The amplified DNA was purified on agarose gel and the purified fragment was sequenced through the generation of two sequences for each sample: one is generated by using forward primer and the other one by using reverse primer. Each sequencing tube was prepared by mixing the purified DNA and TRIS-HCl 5 mM pH 8.0 in order to obtain the concentration requested for the sequencing (depending on the length of the sequence, 2-5 ng/μL).

The sequences were analysed by using BioEdit or BLAST software in order to compare and identify the sequences.

EXAMPLES

Example 1—Method Validation

The gDNA was purified and quantified (Table 1) for the *Vaccinium myrtillus* frozen fruit and its contaminant/related species hereafter reported:

TABLE 1

| Quantification of gDNA extracted for all species tested in the present report. | | | |
|---|---|---|---|
| | Ref. QdL | DNA (ng/μl) | Ratio (260/280) |
| *Vaccinium myrtillus* | 1072/10/12 | 7.9 | 1.61 |
| *Empetrum nigrum* | 1072/10/6 | 29 | 2.07 |
| *Sambucus nigra* | 1072/10/4 | 12 | 2 |
| *Vaccinium macrocarpon* | 1072/10/7 | 3.4 | 2.83 |

TABLE 1-continued

Quantification of gDNA extracted for all
species tested in the present report.

| | Ref. QdL | DNA (ng/μl) | Ratio (260/280) |
|---|---|---|---|
| *Vaccinium oxycoccos* | 1072/10/1 | 6.9 | 1.25 |
| *Vaccinium corymbosum* | 1072/10/3 | 10.2 | 1.23 |

Figure 2:
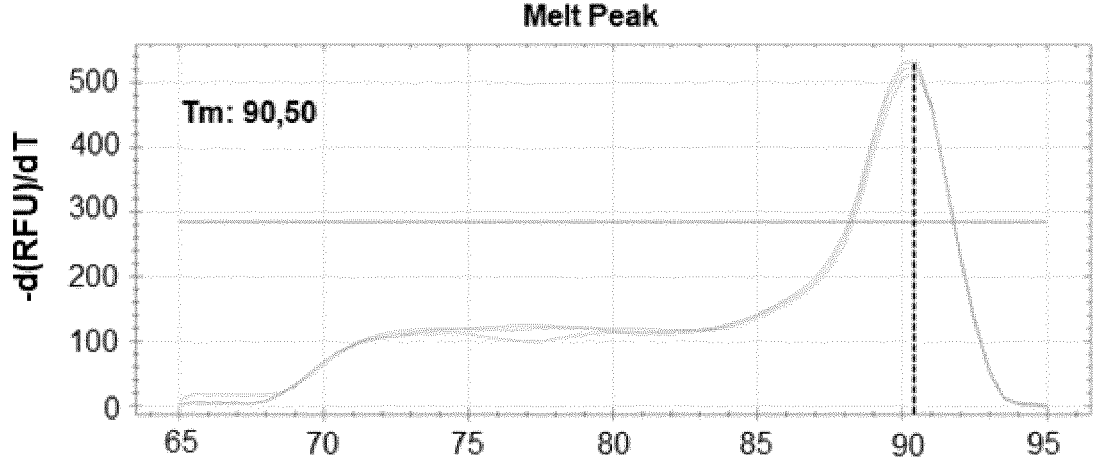
FIG. 2: rt-PCR amplification results (a) and melt curve analysis (b) of genomic DNA isolated from *Vaccinium myrtillus* frozen fruit.
Figure 2:
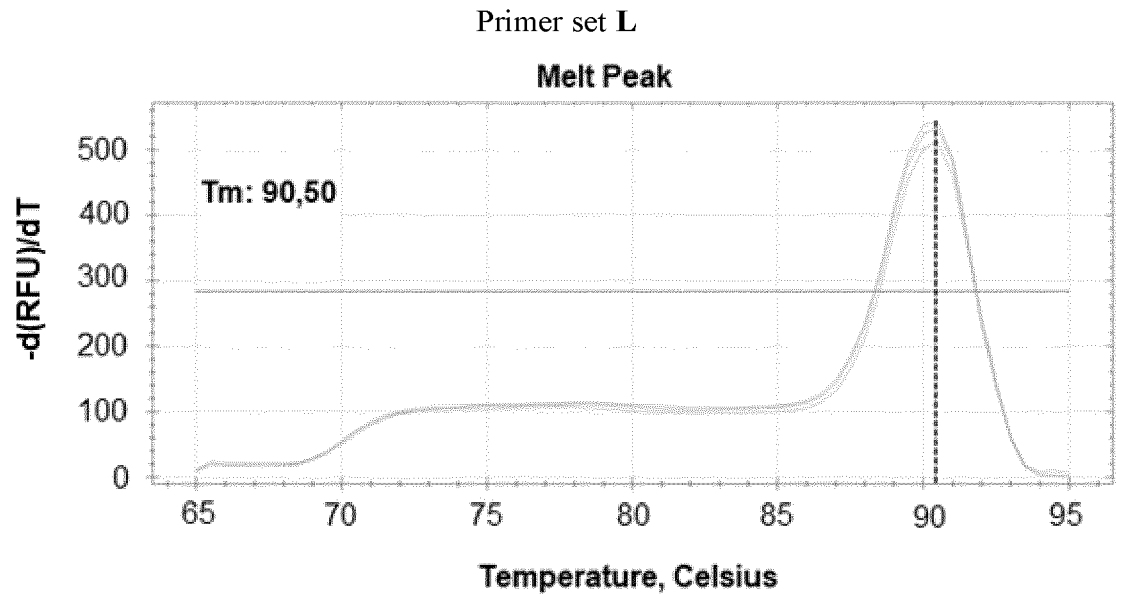
Figure 2:
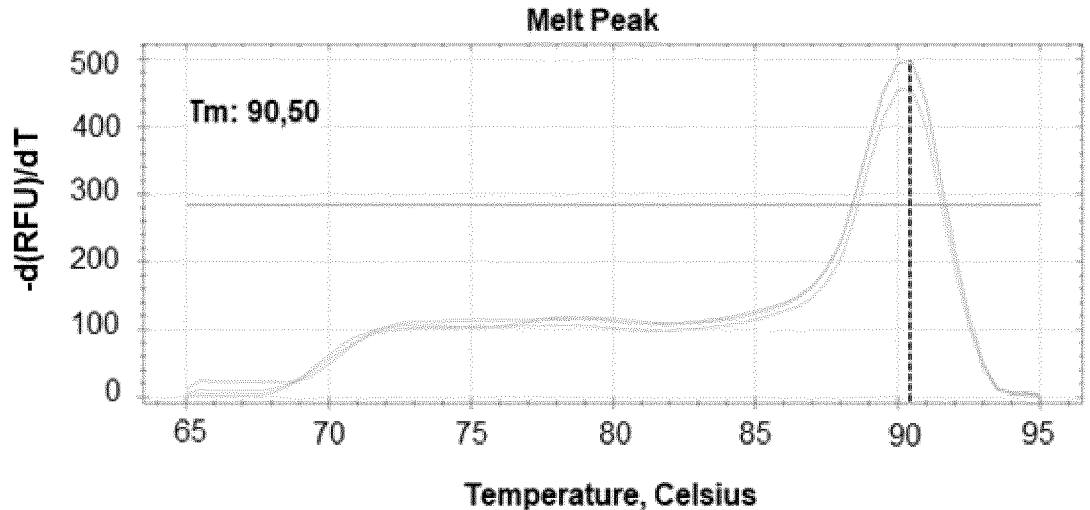
Figure 2:
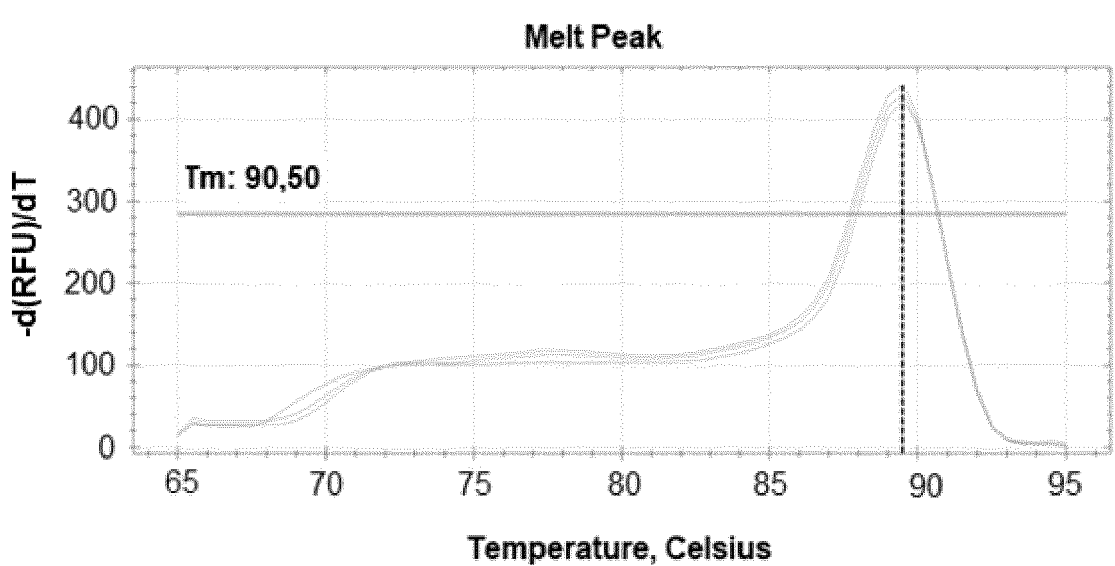

The set-up of rt-PCR reaction parameters, in terms of Cq (quantification cycle) and Tm (melt temperature) peak, were initially evaluated by using the gDNA extracted from *Vaccinium myrtillus* frozen fruit (FIG. 2). The rt-PCR results showed that the designed primers allow the amplification of a single DNA region for all primer set (Tables 2 and 3).

TABLE 2

| Region | Name | Sequence (5'-3') | Tm (° C.) | Amplicon (bp) |
|---|---|---|---|---|
| Large sequence (L) | Vac-ex_LF | CCATCGAGTCTTTGAACGCA | 57.3 | 275 |
| | Vac-ex_LR | CACTTCAGGGTCAAATGGGC | 59.4 | |
| Small sequence (S) | Vac-ex_sF | GCATTGCGTCACCCACTC | 58.2 | 131 |
| | Vac-ex_sR | ACTTGTCGTTGAATGTCCGTCA | 57.3 | |
| Large sequence 2 (L2) | Frw_Large 2 | TTGCAGAATCCCGTGAACCA | 57.3 | 230 |
| | Rev_Small 2 | TTTAGCAACCACCACTTGTCGT | 58.4 | |
| Small sequence 2 (S2) | Frw_Small 2 | TGAAGGCACGTCTGCCTG | 58.2 | 162 |
| | Rev_Small 2 | TTTAGCAACCACCACTTGTCGT | 58.4 | |

TABLE 3

| Primer set | Sample | Cq | Cq Mean | Cq Std. Dev |
|---|---|---|---|---|
| L2 | 1072/10/12 | 25.61 | 25.37 | 0.212 |
| | | 25.28 | | |
| | | 25.21 | | |
| S2 | 1072/10/12 | 26.17 | 25.89 | 0.247 |
| | | 25.70 | | |
| | | 25.80 | | |
| L | 1072/10/12 | 24.88 | 25.11 | 0.203 |
| | | 25.20 | | |
| | | 25.25 | | |
| S | 1072/10/12 | 25.97 | 26.15 | 0.166 |
| | | 26.19 | | |
| | | 26.29 | | |

The rt-PCR was also performed with DNA isolated from *V. myrtillus* contaminant/related species and the results showed that it is possible to distinguish the different DNA by using the primer sets and particularly the small 2 primers (Table 4).

TABLE 4 melt curve peak results

| Sample | Large2 | Small2 | Large | Small |
|---|---|---|---|---|
| *V. myrtillus* | 90.50 | 90.50 | 90.50 | 89.50 |
| *E. nigrum* | 88.50 | 88.00 | 90.50 | 89.00/89.50 |
| *S. nigra* | 88.50 | 87.50 | 89.50 | 87.50 |
| *V. oxycoccos* | 91.00 | 91.00 | 91.00 | 89.50/90.00 |

TABLE 4-continued melt curve peak results

| Sample | Large2 | Small2 | Large | Small |
|---|---|---|---|---|
| *V. corymbosum* | 89.00 | 89.00 | 89.00 | 88.00 |
| *V. macrocarpon* | 91.50 | 91.50 | 91.00 | 90.50 |

Figure 3:
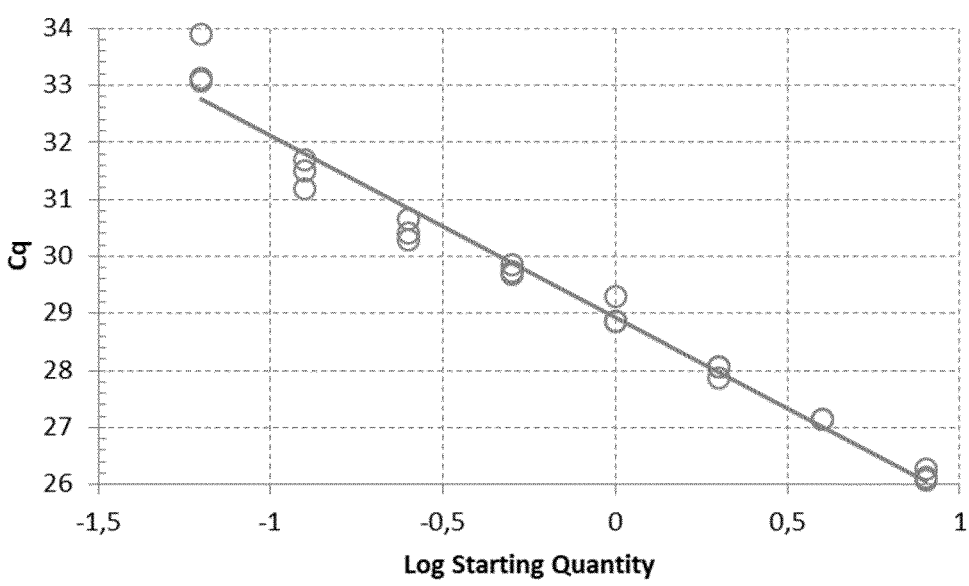
FIG. 3: Standard curve analysis for *Vaccinium myrtillus.*

The linearity of the amplification curve was also evaluated with the standard curve PP-6T generation for *Vaccinium myrtillus* by using the small 2 primer set (FIG. 3). It is possible to see that the linearity has been ensured in the tested range of concentration (almost 0.0625-8.00 ng/μl).

In order to improve the method capability to distinguish between *Vaccinium myrtillus* and contaminant/related species, the rtPCR was conducted with the Minor Groove Binding-Probe (M-FAM-SEQ ID NO: 13) specifically designed to enable the amplification of *V. myrtillus* sequences.

In a comparative experiment, the rtPCR was conducted with simultaneous use of the Minor Groove Binding-Probes SEQ ID NO:13 (M-FAM) and SEQ ID NO:14 (E-HEX).

To test the probe-based method different subsets of experiments have been carried out, summarized in the table below.

TABLE 5

Figure 4:
FIG. 4: Probe-based rt-PCR amplification with M-FAM probe specific for *V. myrtillus* NTC: negative control.
Figure 5:
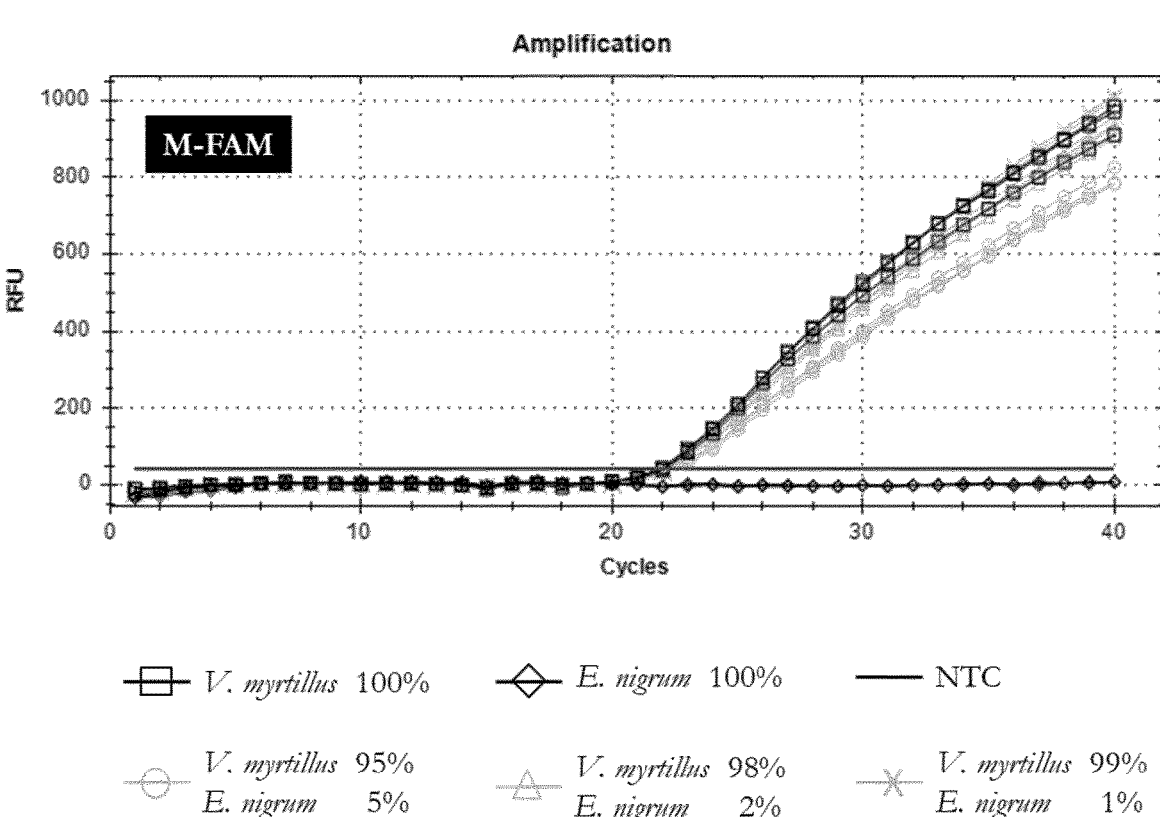
FIG. 5: (a) Probe-based rt-PCR amplification with M-FAM probe specific for *V. myrtillus* in a mixed samples with a ratio reported in the legend. NTC: negative control; (b) Probe-based rt-PCR amplification with E-HEX probe specific for *E. nigrum* in a mixed samples with a ratio reported in the legend. NTC: negative control.
Figure 5:
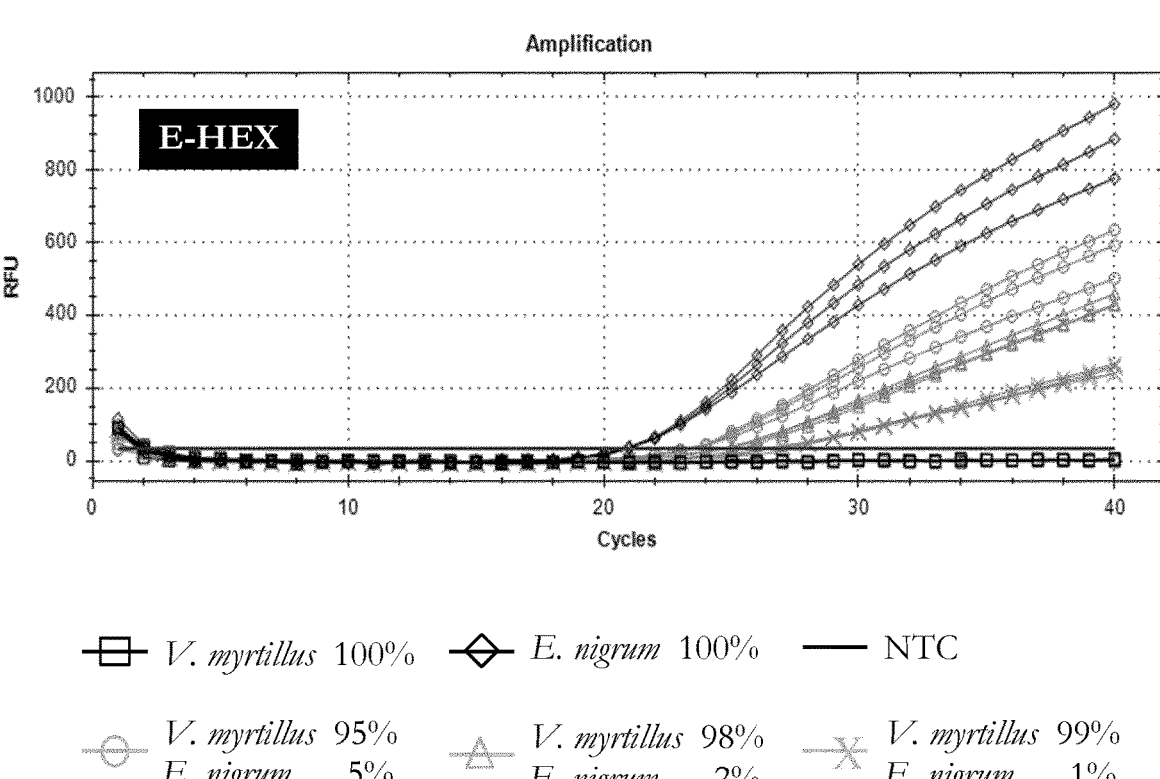

| Probe | Sample | Expected result | Result |
|---|---|---|---|
| M-FAM | *V. myrtillus* | Amplification of *V. myrtillus* | FIG. 4 |
| | *E. nigrum* | | |
| | *S. nigra* | | |
| | *V. oxycoccos* | | |
| | *V. corymbosum* | | |
| | *V. macrocarpon* | | |
| M-FAM | *V. myrtillus* 100% | No Amplification | FIG. 5(a) |
| | *E. nigrum* 100% | Amplification | |
| | *V. myrtillus* 95% | Proportional | |
| | *E. nigrum* 5% | amplification with | |
| | *V. myrtillus* 98% | the percentage of | |
| | *E. nigrum* 2% | *V. myrtillus* | |
| | *V. myrtillus* 99% | | |
| | *E. nigrum* 1% | | |

TABLE 5-continued

| Probe | Sample | Expected result | Result |
|---|---|---|---|
| E-HEX | V. myrtillus 100%<br>E. nigrum 100%<br>V. myrtillus 95%<br>E. nigrum 5%<br>V. myrtillus 98%<br>E. nigrum 2%<br>V. myrtillus 99%<br>E. nigrum 1% | No Amplification<br>Amplification<br>Proportional<br>amplification with<br>the percentage of<br>E. nigrum | FIG. 5(b) |

Figure 6:
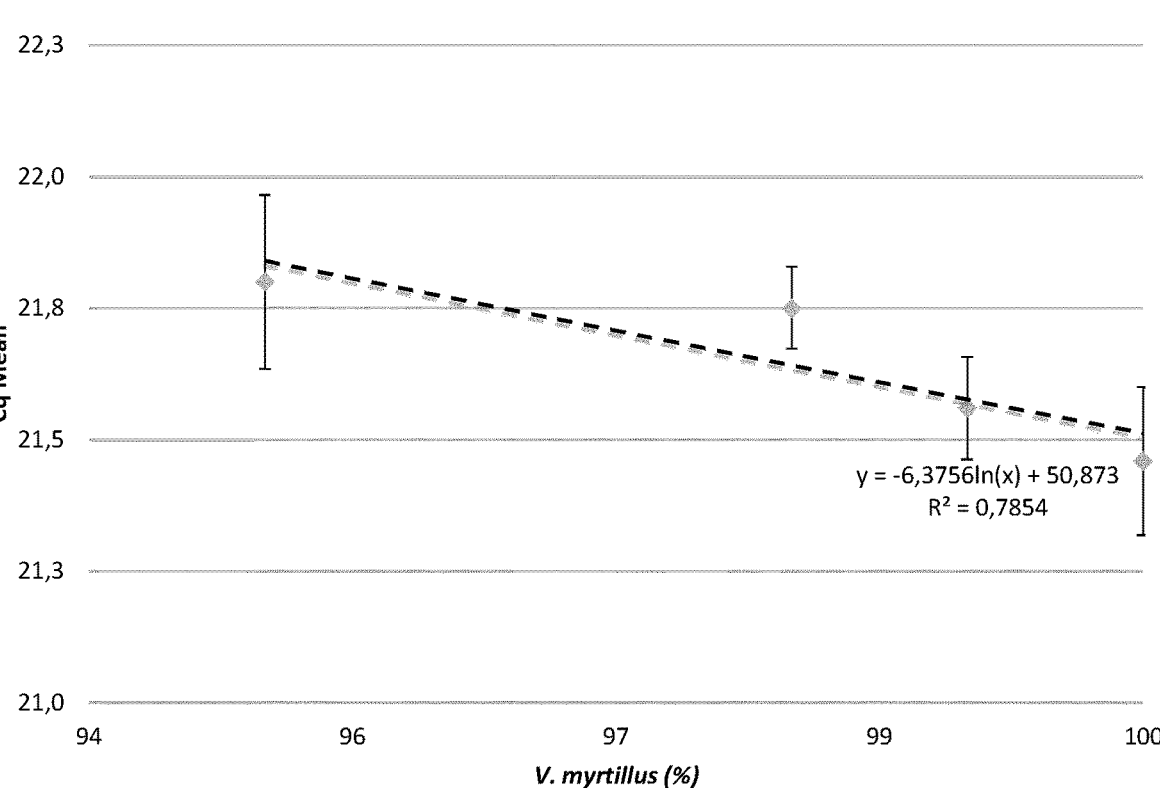
FIG. 6: Correlation between Cq Mean and percentage of target species for *V. myrtillus*.

The amplification results were proportional to the content of the target species (FIG. 6).

Example 2—*Vaccinium myrtillus* Dry-Extract Residual DNA Identification

Figure 7:
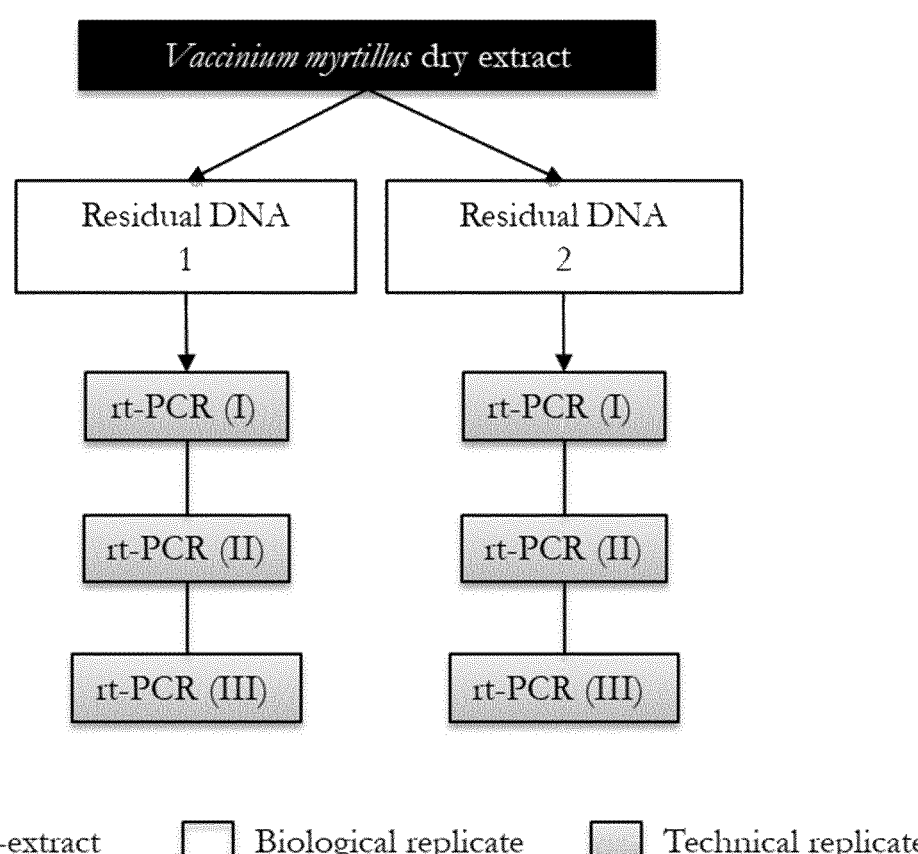
FIG. 7: Experimental scheme used for rt-PCR analysis of dry extract samples.

For each sample, two independent isolations of residual DNA were performed (biological replicates) and for each extracted DNA three technical replicates were tested, FIG. 7.

Figure 8:
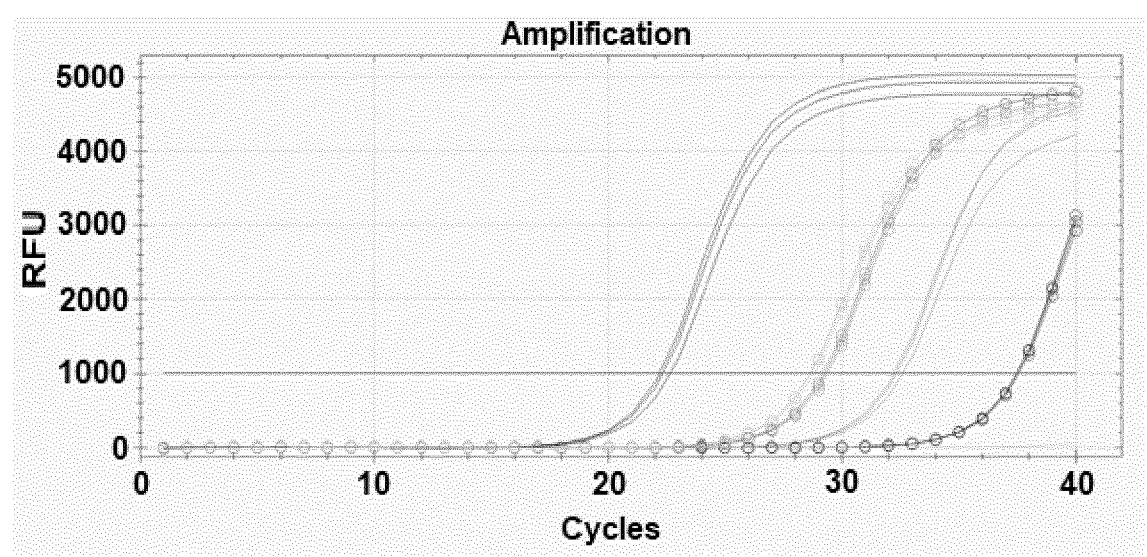
FIG. 8: rt-PCR amplification of residual DNAs isolated from *Vaccinium myrtillus* dry-extract samples. The positive control is the gDNA extracted from *Vaccinium myrtillus* frozen fruit. a) Primer set L; b) Primer set S.
Figure 8:
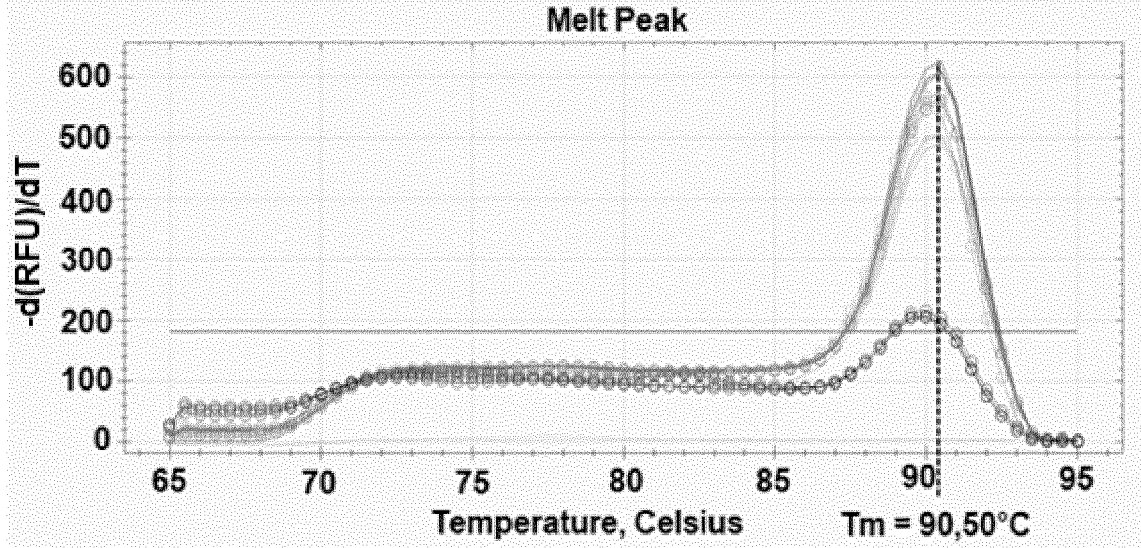
Figure 8:
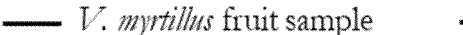
Figure 8:
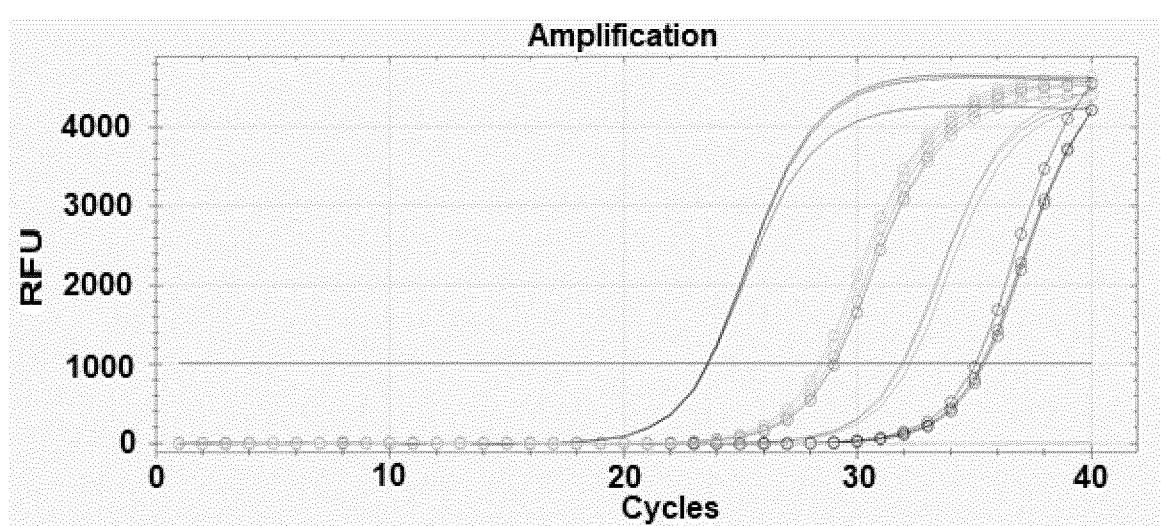
Figure 8:
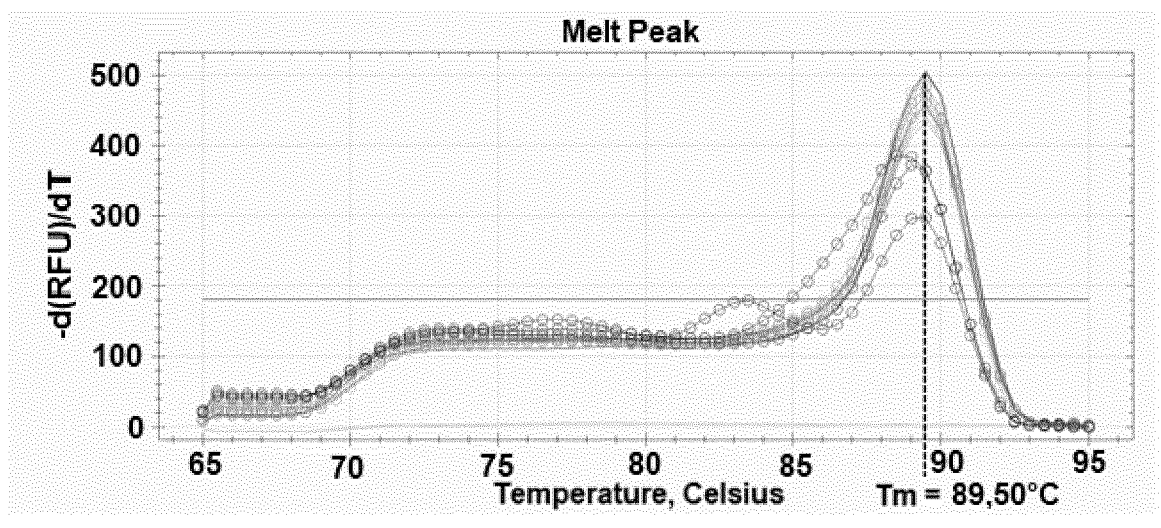
Figure 8:

The whole procedure was initially performed on four samples: 32549/H76, 32549/1H80, 32549/1H83, 32549/1H84. After the residual DNA isolation and quantification (Table 6), these samples were analysed for their rt-PCR amplification characteristics (Cq and Tm) compared with that of positive control (FIG. 8 and Table 7).

TABLE 6

| | | Residual DNA quantification | |
|---|---|---|---|
| Sample | Biological<br>replicate | DNA<br>(ng/μL) | Ratio<br>(260/280) |
| 32549/H76 | 1 | 0 | 3.5 |
| | 2 | 1 | 1.25 |
| 32549/H80 | 1 | 0 | 0 |
| | 2 | 1.1 | 0.55 |
| 32549/H83 | 1 | 0.7 | 1.4 |
| | 2 | 0 | 2 |
| 32549/H84 | 1 | 10.3 | 1.41 |
| | 2 | 10.3 | 1.38 |

TABLE 7

| | | rt-PCR Summary results | | |
|---|---|---|---|---|
| Sample | DNA<br>(ng/μL) | Cq. Mean | Cq. Std. Dev | Melt Temp |
| 32549/H76_2 | 1.0 | 32.05 | 0.180 | 89.50 |
| 32549/H83_1 | 0.7 | 35.26 | 0.181 | 89.00 |
| 32549/H84_1 | 10.3 | 28.96 | 0.119 | 89.50 |
| 32549/H84_2 | 10.6 | 28.44 | 0.092 | 89.50 |
| Negative ctrl | 0.0 | None | None | None |
| Positive ctrl | 24.8 | 23.60 | 0.040 | 89.50 |

The results of rt-PCR amplification with all samples showed that:

the DNA was amplified for the positive control as well as for all tested samples;

the negative control (no DNA) showed no amplification signal;

positive control and samples showed equal values for Tm peaks.

This result indicates that the amplicons have the same characteristics in terms of length and/or nucleotide bases composition.

Moreover the Cq results are correlated with the DNA amount tested, meaning that the amplification is specific for the selected target.

Figure 9:
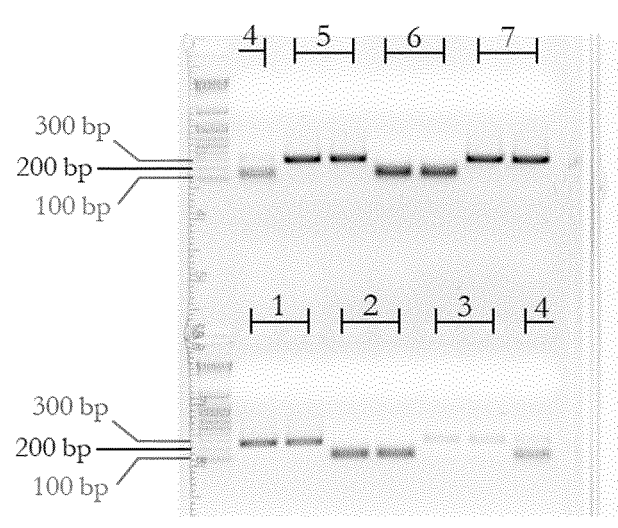
FIG. 9: Agarose gel analysis of rt-PCR amplicons.
Figure 9:
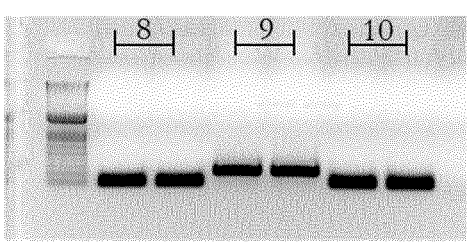
Figure 10:
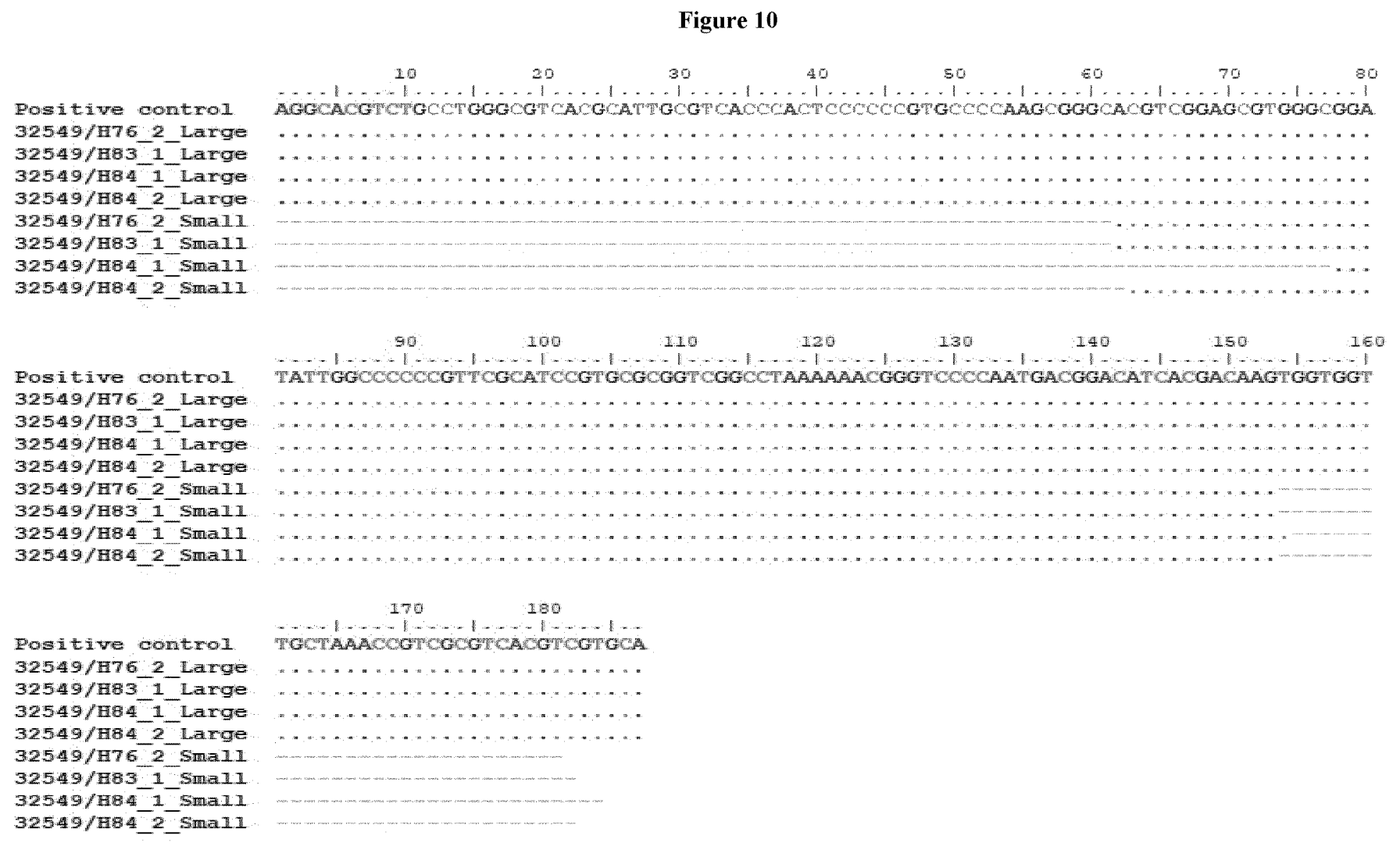

To verify if the generated amplicons have the same sequence of the positive control, all amplified sequences were purified on agarose gel (FIG. 9) and the purified fragments were sequenced (FIG. 10).

The agarose gel analysis confirmed the differences of the amplicons length: the fragment generated with primer set S shows a length of about 130 bp, while the fragment generated with primer set L shows a length of about 270 bp. Moreover, from gel agarose analysis it is possible to see also the presence of unspecific rt-PCR products, as in FIG. 9, lane 4 for the sample 32549/H83_1 where two bands are visible, in good accord with Tm peak results (FIG. 8, b).

All generated sequences were aligned by considering only the portion with high quality sequencing parameters. The sequencing results (FIG. 10) showed that all amplicon sequences (small and large) are identical to the sequence of the *Vaccinium myrtillus* standard reference.

Example 3—*Vaccinium myrtillus* 36% Dry Ethanolic Extract (E. ET.) Residual DNA Identification The residual DNA analysis was also performed on samples with Indena code 9042202, MIRTILLO (V. *MYRTILLUS*) E. ET. 36% after the dry-powder mixing phase, 32788/M1, 32786/M2, 32788/M2. The previous samples 32549/H76, 32549/H80 and 32549/H83 were tested again as control samples.

In order to optimize the purification procedure, after the first step of DNA purification the isolated residual DNA was processed with ReliaPrep™ Kit (Promega). The results in terms of DNA quantity (ng/μL) and quality (260/280 ratio) on the two purification steps (Table 8) revealed that the concentration as well as the purification are better introducing the second step.

TABLE 8

| | Residual DNA quantification - E. ET. 36% | | | |
|---|---|---|---|---|
| | I purification | | II purification | |
| Sample | DNA<br>(ng/μL) | Ratio<br>(260/280) | DNA<br>(ng/μL) | Ratio<br>(260/280) |
| 32549/H76 | 0 | — | 2.3 | 1.77 |
| 32549/H80 | 0 | 2 | 0.2 | 0.5 |
| 32549/H83 | 0 | 0.84 | 2.1 | 1.75 |
| 32788/M1 | 1.2 | 0.71 | 3.4 | 1.55 |
| 32786/M2 | 0 | — | 2.5 | 1.67 |
| 32788/M2 | 0.3 | 0.75 | 3.6 | 1.5 |

Figure 11:
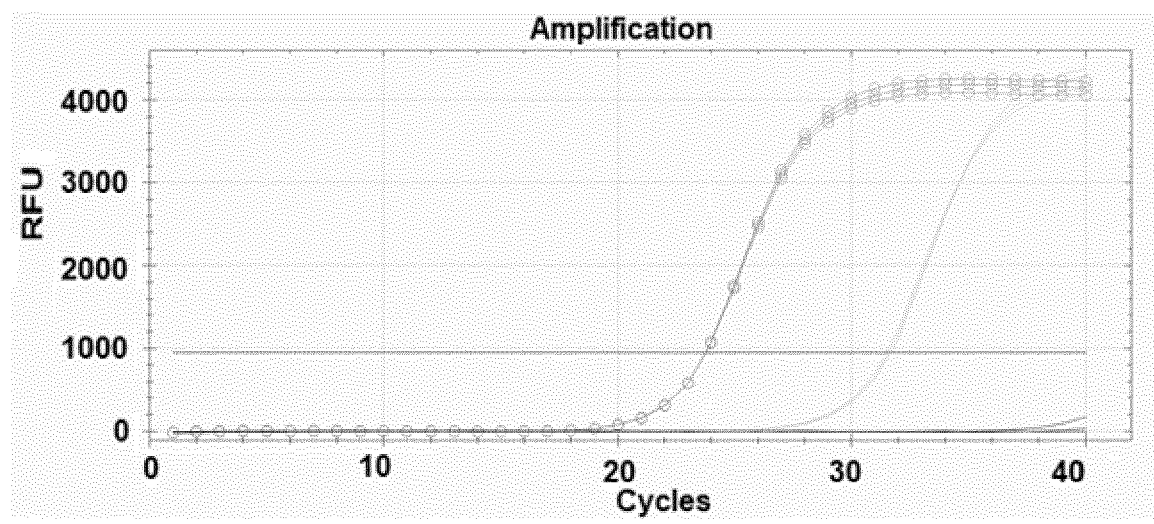
FIG. 11: rt-PCR of *Vaccinium myrtillus* E. ET. 36%. Amplification and melt curves.
Figure 11:
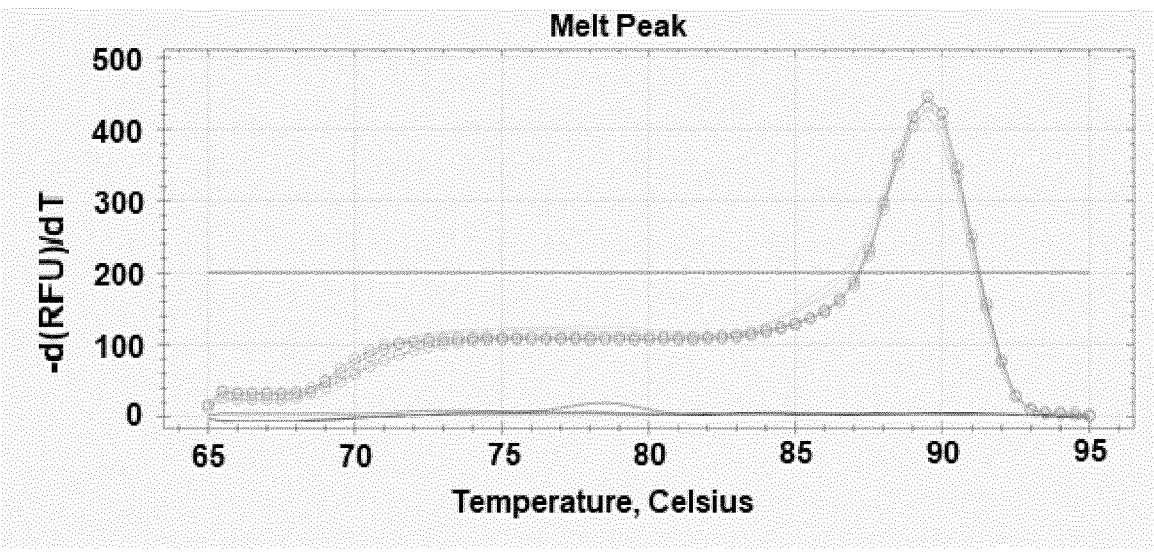
Figure 11:
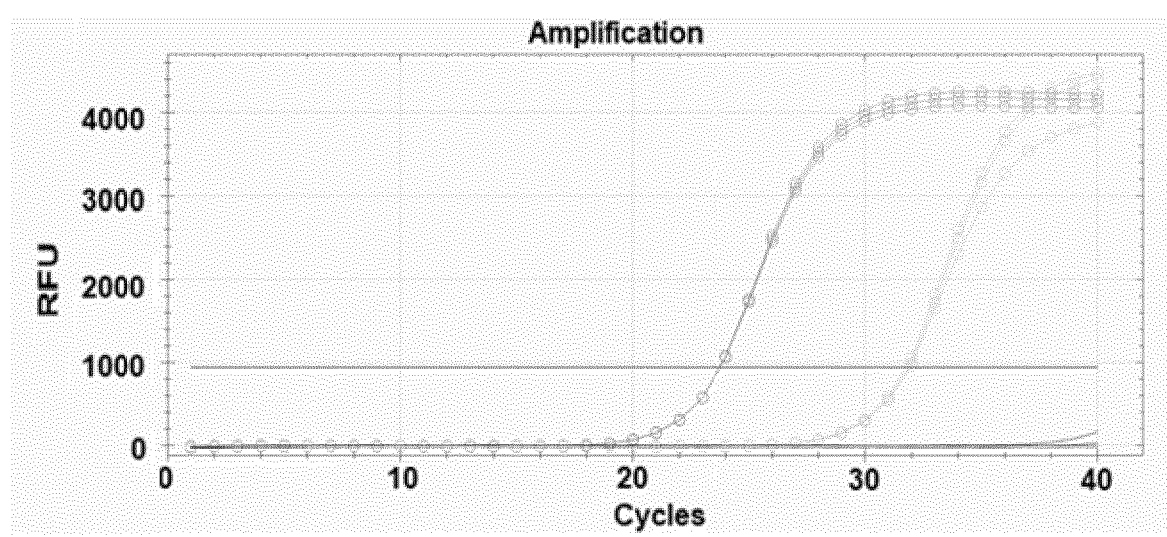
Figure 11:
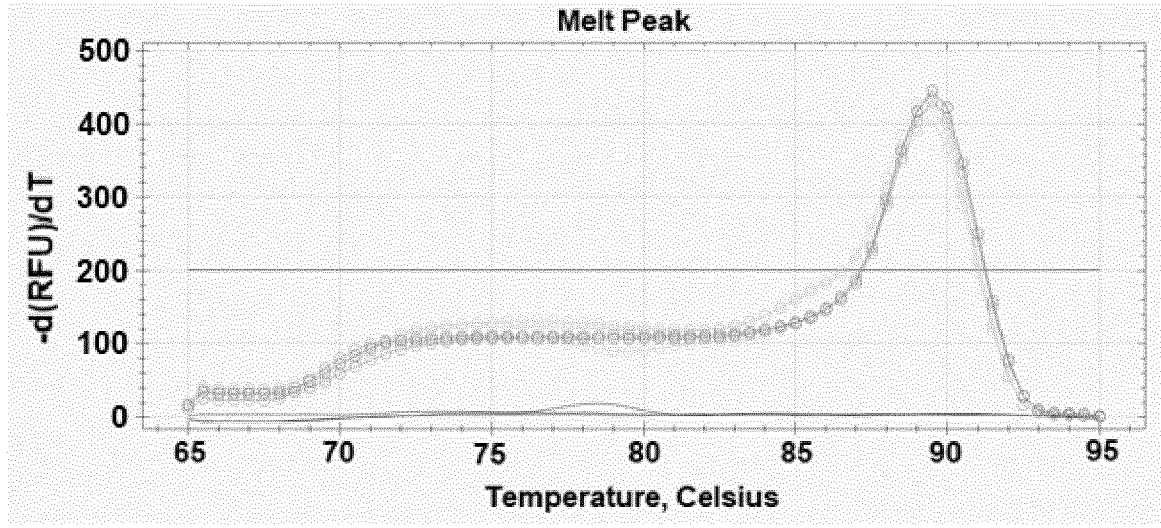
Figure 11:
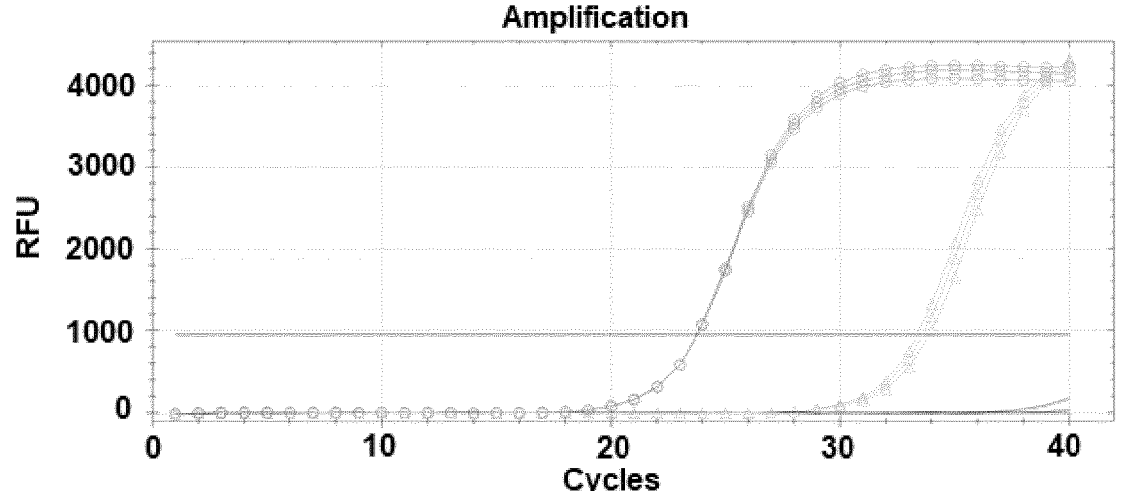
Figure 11:
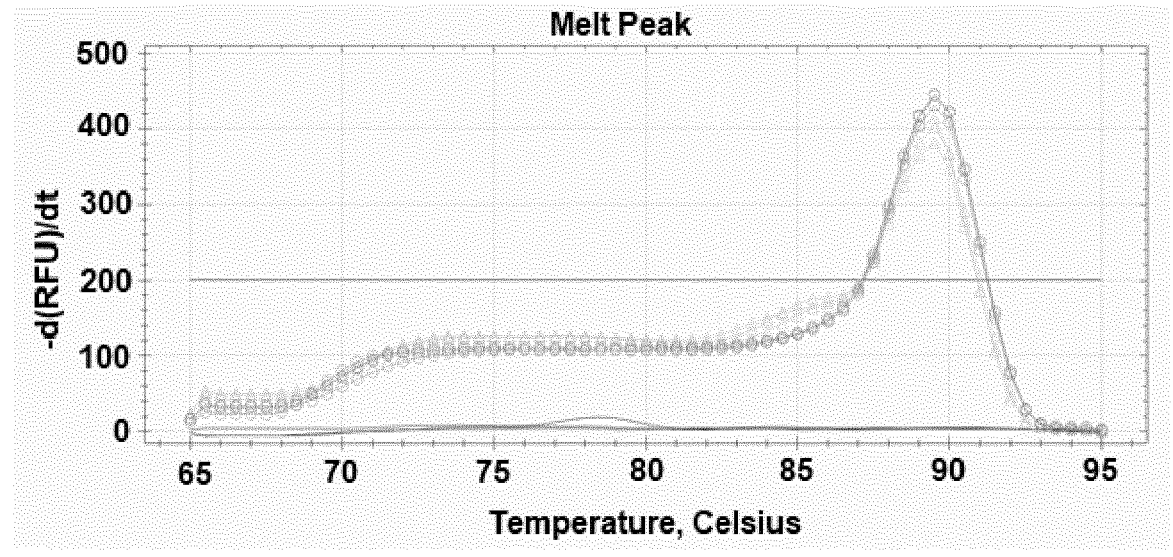
Figure 11:
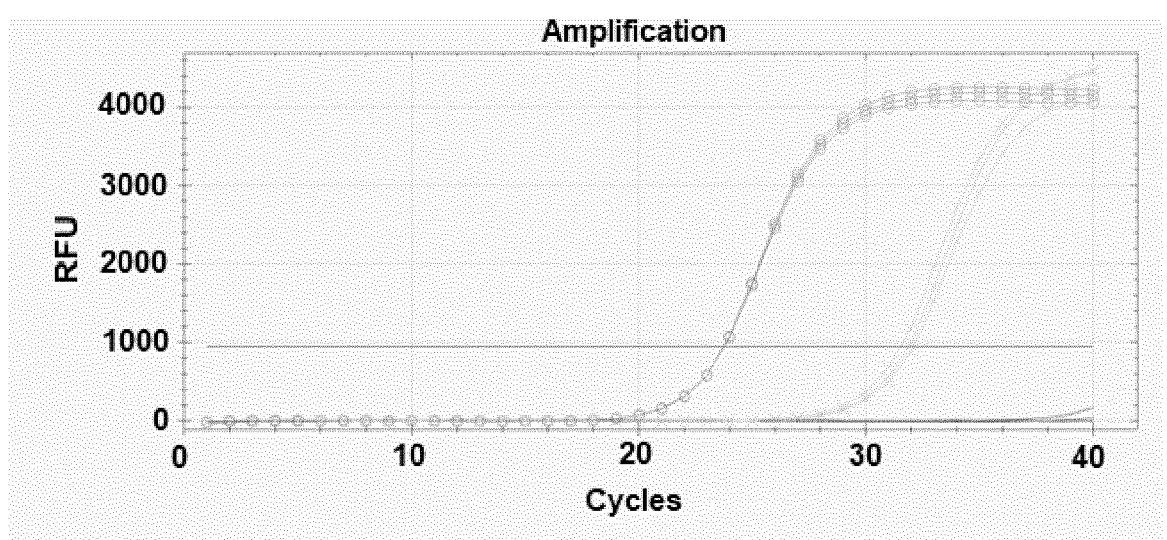
Figure 11:
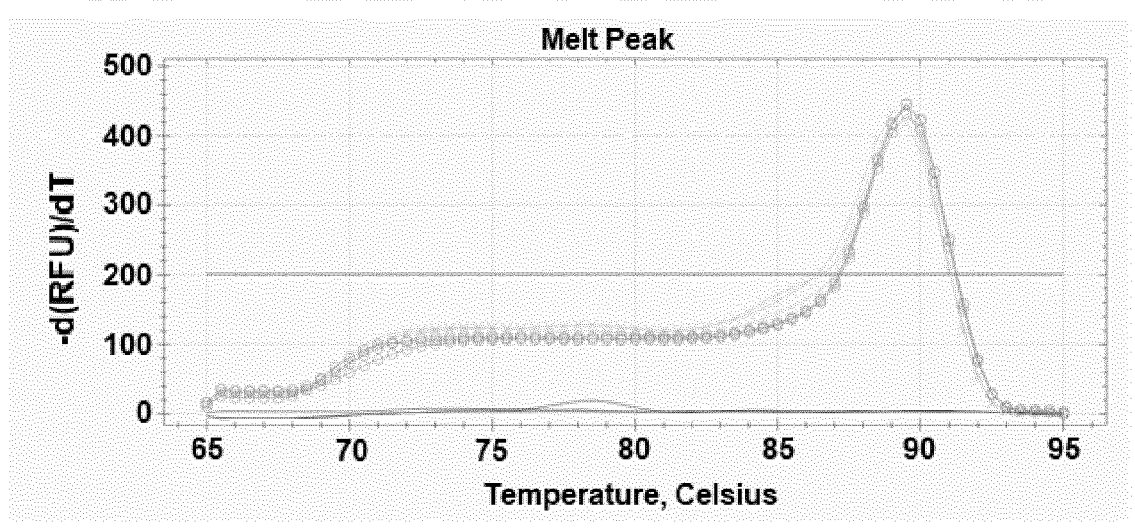
Figure 11:
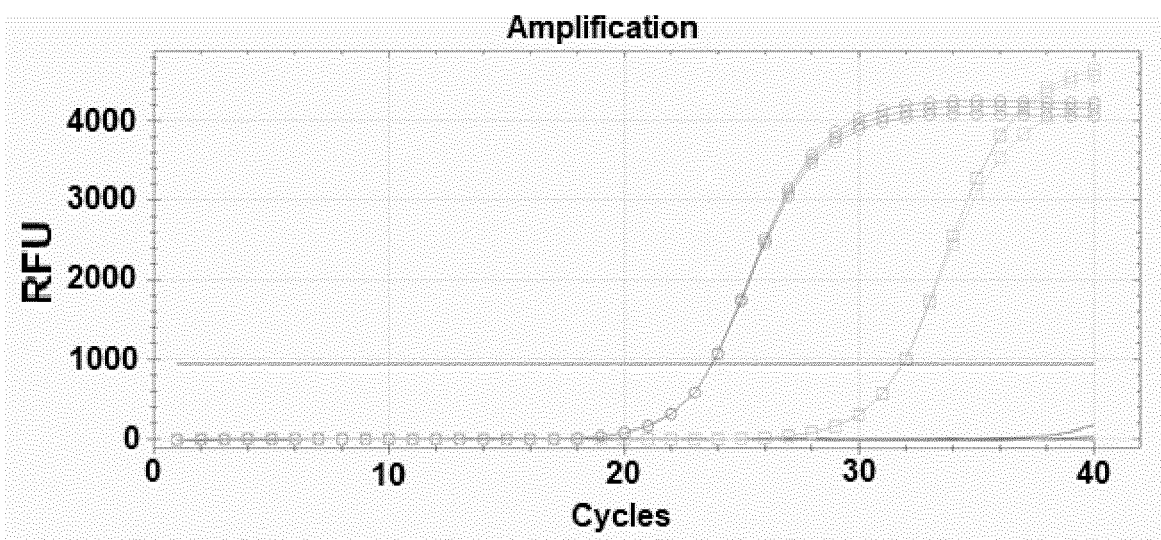
Figure 11:
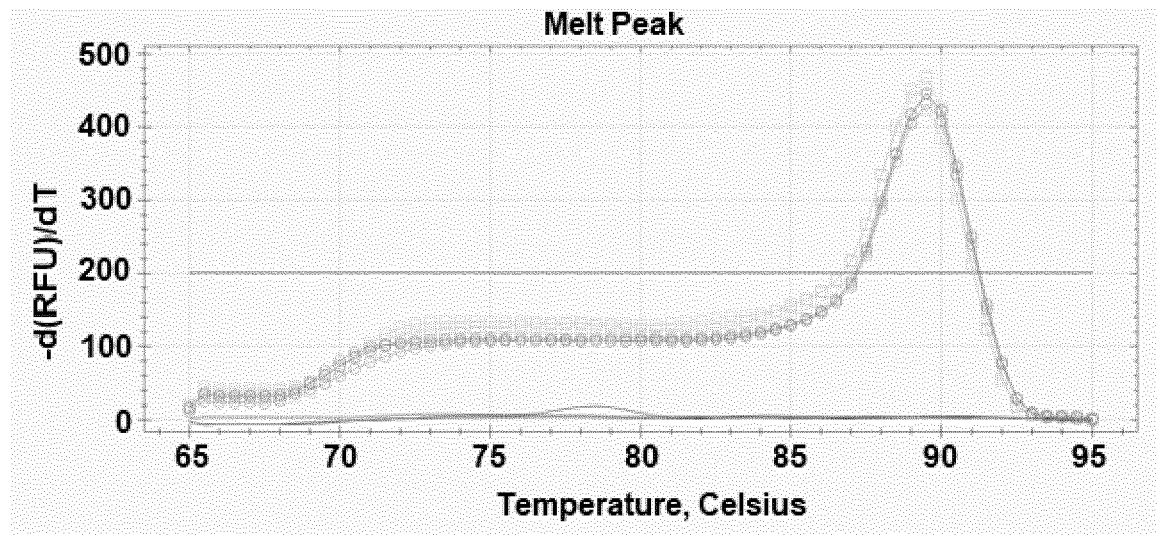
Figure 11:
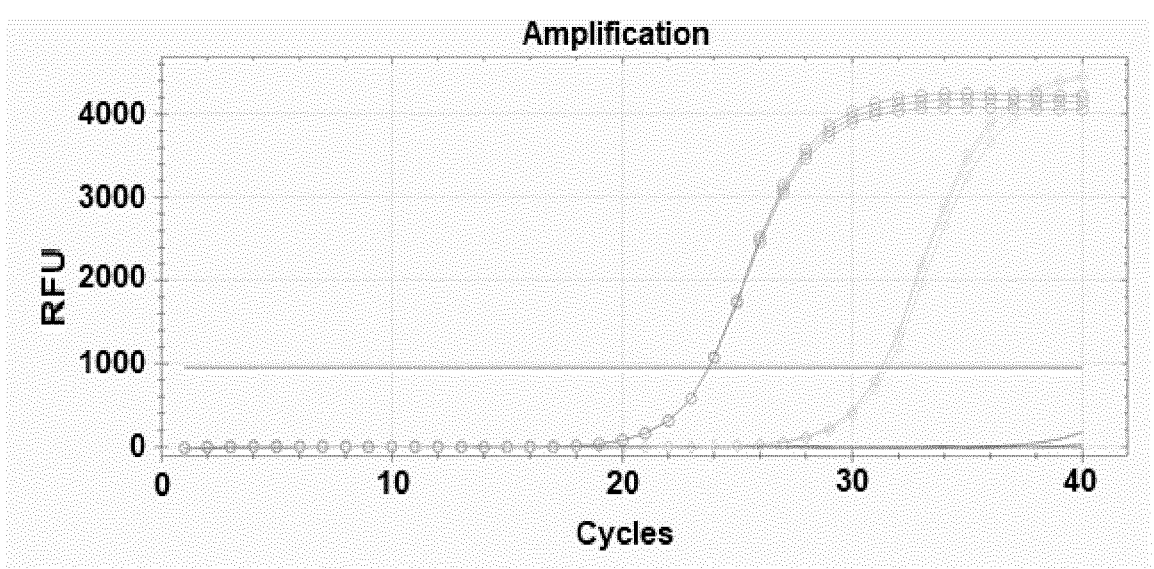
Figure 11:
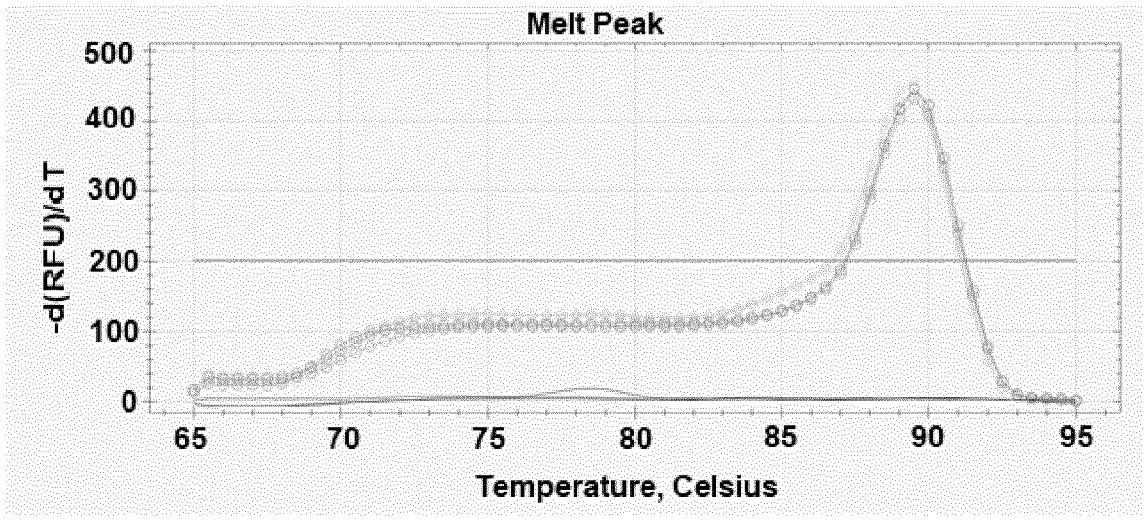
Figure 12:
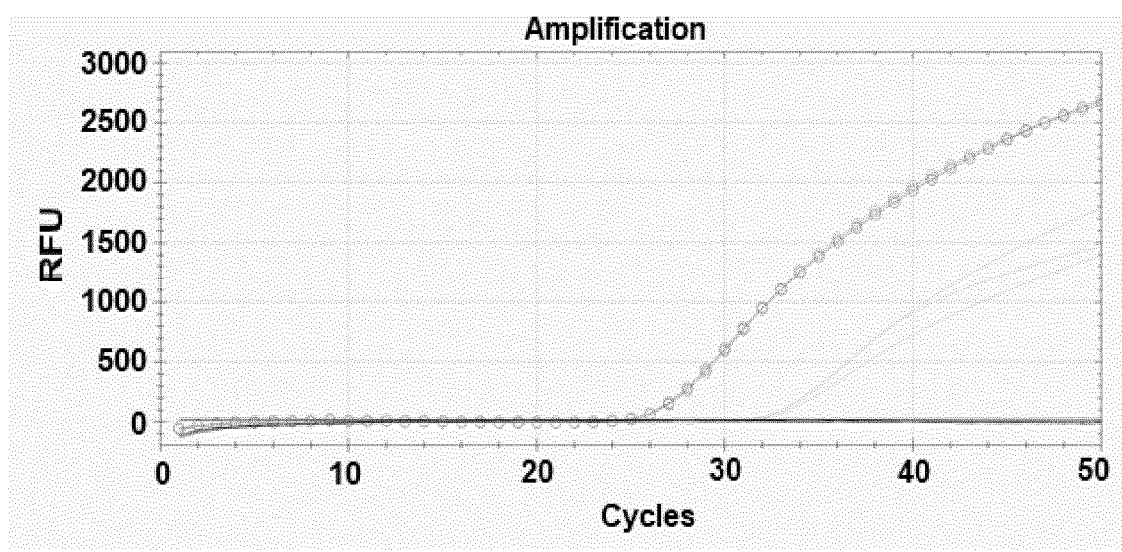
FIG. 12: rt-PCR of *Vaccinium myrtillus* E. ET. 36% with probe-based method. PTC: positive control (gDNA extracted from frozen fruit of *V. myrtillus*); NTC: negative control.
Figure 12:
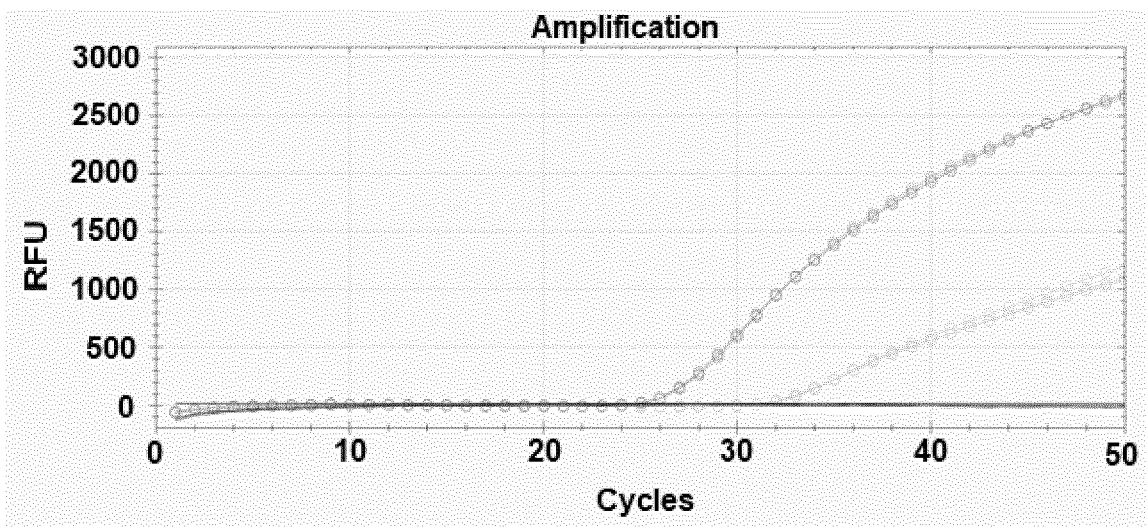
Figure 12:
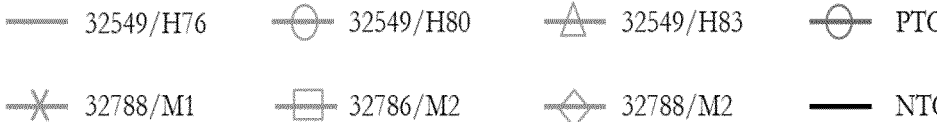
Figure 12:
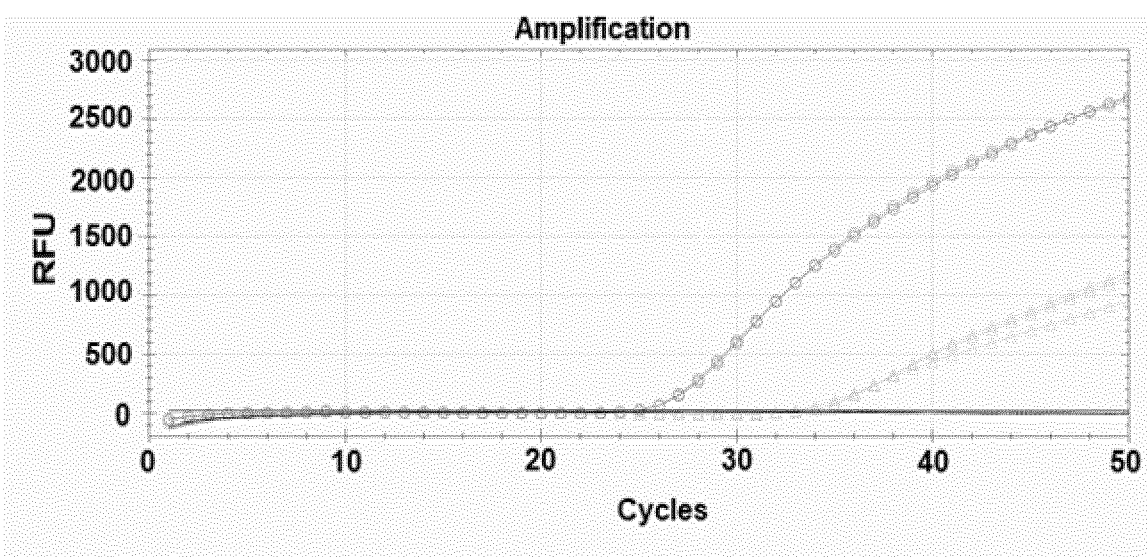
Figure 12:
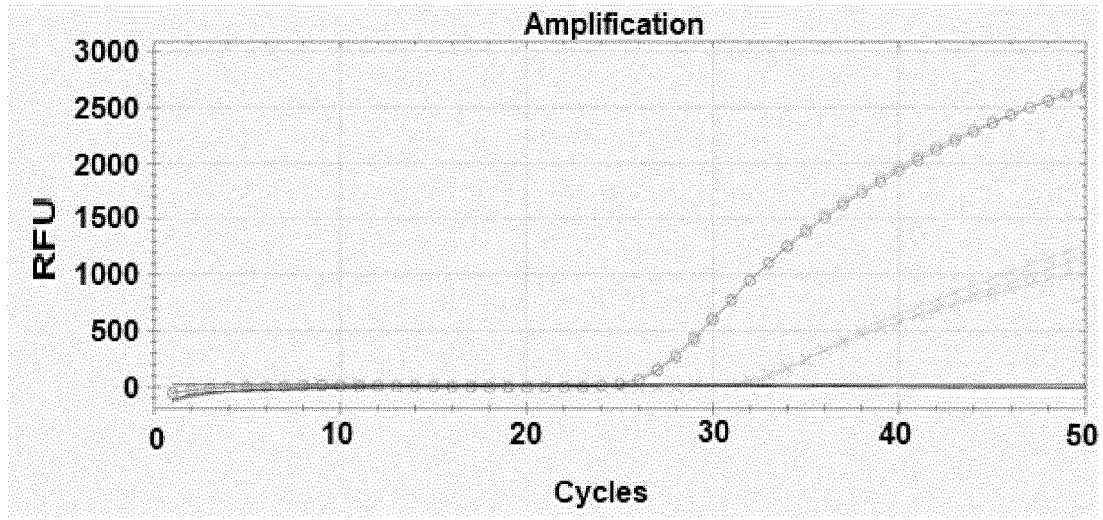
Figure 12:
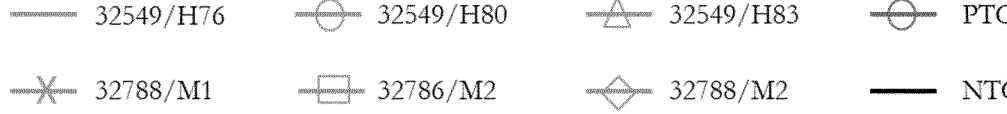
Figure 12:
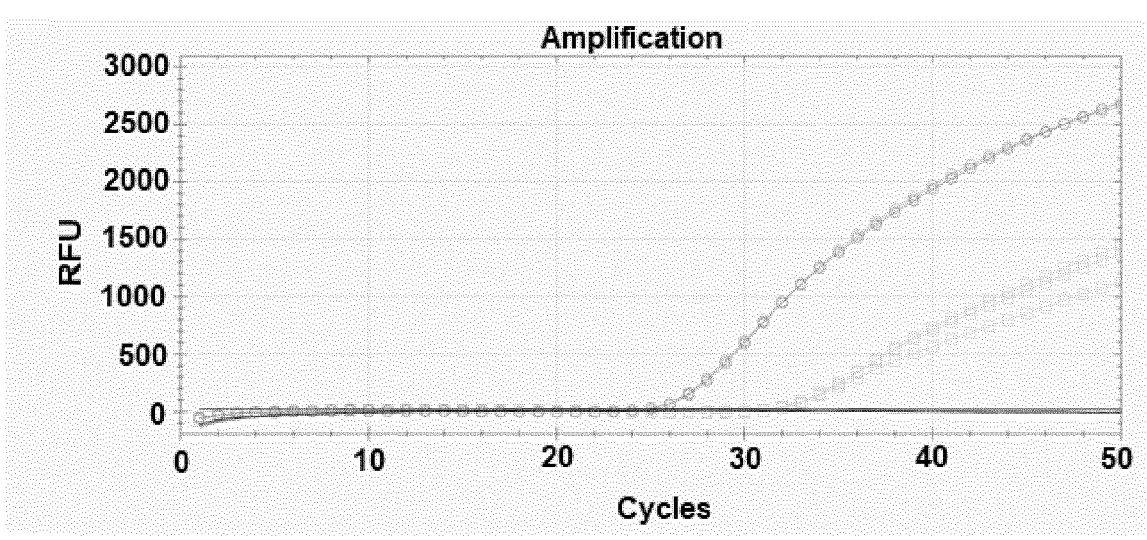
Figure 12:
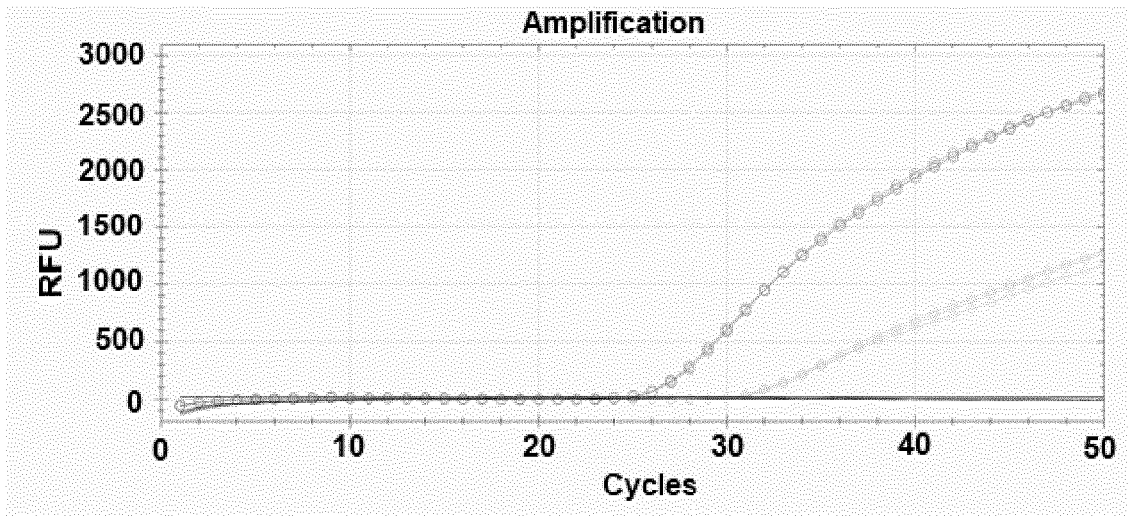
Figure 12:
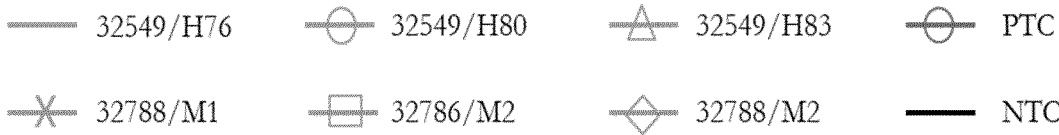

The rt-PCR analysis was performed by using SYBR green (FIG. 11) and probe-based methods (FIG. 12), according to the protocols described above.

The results indicate that:

(a) all tested samples showed the same Tm peak of the positive control (FIG. 11 and Table 9) when analysed with SYBR green method:

TABLE 9

| | rt-PCR Summary results, SYBR green method - E. ET. 36% | | | |
|---|---|---|---|---|
| Sample | DNA<br>(ng/μL) | Cq. Mean | Cq. Std. Dev | Melt Temp |
| 32549/H76 | 2.3 | 31.59 | 0.099 | 89.50 |
| 32549/H80 | 0.2 | 31.87 | 0.107 | 89.50 |
| 32549/H83 | 2.1 | 33.61 | 0.276 | 89.50 |

TABLE 9-continued rt-PCR Summary results, SYBR green method - E. ET. 36%

| Sample | DNA (ng/µL) | Cq. Mean | Cq. Std. Dev | Melt Temp |
|---|---|---|---|---|
| 32788/M1 | 3.4 | 31.85 | 0.286 | 89.50 |
| 32786/M2 | 2.5 | 31.88 | 0.011 | 89.50 |
| 32788/M2 | 3.6 | 31.36 | 0.144 | 89.50 |
| Negative ctrl | 0 | 0 | 0 | None |
| Positive ctrl | 24.8 | 23.75 | 0.016 | 89.50 |

(b) all tested samples were detected with the probe specific for the sequence of *V. myrtillus* (FIG. 12 and Table 10) when analysed with probe-based method.

TABLE 10 rt-PCR Summary results, Probe-based method - E. ET. 36%

| Sample | DNA (ng/µL) | Cq. Mean | Cq. Std. Dev |
|---|---|---|---|
| 32549/H76 | 2.3 | 31.52 | 0.306 |
| 32549/H80 | 0.2 | 31.38 | 0.073 |
| 32549/H83 | 2.1 | 33.44 | 0.326 |
| 32788/M1 | 3.4 | 31.10 | 0.098 |
| 32786/M2 | 2.5 | 31.52 | 0.156 |
| 32788/M2 | 3.6 | 30.53 | 0.197 |
| Negative ctrl | 0 | 0 | 0 |
| Positive ctrl | 7.45 | 24.84 | 0.177 |

Example 4—Kit for the Analysis

The kit is composed by:

One 1.5 ml tube containing all reagents necessary to perform the analysis (DNA Polymerase, dNTPs, Buffer, Probe chemistry, Primers and Probe)

One 1.5 ml tube containing the positive control (DNA of *Vaccinium myrtillus*)

One 1.5 ml tube containing the negative control DNA (Nuclease-free water)

The kit can be used with all commercially available Real-time PCR System (es: BioRad CFX96™, BioRad CFX96™, bCube®, Roche LightCycler® 480, etc)

List of sequences

Nucleic acid fragments

```
GCATTGCGTCACCCACTCCCCCCGTGCCCCAAGCGGGCACGTCGGAGCG
TGGGCGGATATTGGCCCCCCGTTCGCATCCGTGCGCGGTCGGCCTAAAA
AACGGGTCCCCAATGACGGACATCACGACAAGT (SEQ ID NO: 1)

TGAAGGCACGTCTGCCTGGGCGTCACGCATTGCGTCACCCACTCCCCCC
GTGCCCCAAGCGGGCACGTCGGAGCGTGGGCGGATATTGGCCCCCCGTT
CGCATCCGTGCGCGGTCGGCCTAAAAAACGGGTCCCCAATGACGGACAT
CACGACAAGTGGTGGTTGCTAAA (SEQ ID NO: 2)

TTGCAGAATCCCGTGAACCATCGAGTCTTTGAACGCAAGTTGCGCCTGA
AGCCATTAGGTTGAAGGCACGTCTGCCTGGGCGTCACGCATTGCGTCAC
CCACTCCCCCCGTGCCCCAAGCGGGCACGTCGGAGCGTGGGCGGATATT
GGCCCCCCGTTCGCATCCGTGCGCGGTCGGCCTAAAAAACGGGTCCCCA
ATGACGGACATCACGACAAGTGGTGGTTGCTAAA (SEQ D NO: 3)

CCATCGAGTCTTTGAACGCAAGTTGCGCCTGAAGCCATTAGGTTGAAGG
CACGTCTGCCTGGGCGTCACGCATTGCGTCACCCACTCCCCCCGTGCCC
CAAGCGGGCACGTCGGAGCGTGGGCGGATATTGGCCCCCCGTTCGCATC
CGTGCGCGGTCGGCCTAAAAAACGGGTCCCCAATGACGGACATCACGAC
AAGTGGTGGTTGCTAAACCGTCGCGTCACGTCGTGCATGCCATCGTTTG
TTGCGGGTTGGCCCATTTGACCCTGAAGTG (SEQ ID NO: 4)
```

Primers

| "S" | | |
|---|---|---|
| F | GCATTGCGTCACCCACTC | (SEQ ID NO: 5) |
| R | ACTTGTCGTGATGTCCGTCA | (SEQ ID NO: 6) |
| "S2" | | |
| F | TGAAGGCACGTCTGCCTG | (SEQ ID NO: 7) |
| R | TTTAGCAACCACCACTTGTCGT | (SEQ ID NO: 8) |
| "L2" | | |
| F | TTGCAGAATCCCGTGAACCA | (SEQ ID NO: 9) |
| R | TTTAGCAACCACCACTTGTCGT | (SEQ ID NO: 10) |
| "L" | | |
| F | CCATCGAGTCTTTGAACGCA | (SEQ ID NO: 11) |
| R | CACTTCAGGGTCAAATGGGC | (SEQ ID NO: 12) |

Probes

```
M-FAM
ACGTCGGAGCGTGGGC (SEQ ID NO: 13)

E-HEX
TAGGGCGGGTAAGTGAGT (SEQ ID NO: 14)
```

---

The invention claimed is:

1. A method for the identification of *Vaccinium myrtillus* (*V. myrtillus*) in a botanical composition, which comprises detecting from a sample thereof, by means of PCR-amplification, a *V. myrtillus* nucleic acid fragment spanning a genomic region comprising the internal transcribed spacer 1, 5.8S ribosomal RNA genomic region and the internal transcribed spacer 2, said method comprising:

(a) isolating nucleic acids from said sample;

(b) conducting a real-time PCR on the isolated nucleic acid, using:

a set of primers selected from the group consisting of:

(i) SEQ ID NO:5 and SEQ ID NO:6;

(ii) SEQ ID NO:7 and SEQ ID NO:8;

(iii) SEQ ID NO:9 and SEQ ID NO:10;

(iv) SEQ ID NO:11 and SEQ ID NO:12; and a probe annealing within the nucleic acid region amplified by the primers, said probe consisting of the sequence SEQ ID NO:13;

(c) determining the presence of the amplification product, whereby the detection of the amplification product is indicative of the presence of *Vaccinium myrtillus* in the botanical composition.

2. The method of claim 1, wherein the set of primers (i) is used in step (b).

3. The method of claim 1, wherein said rt-PCR is conducted under the following conditions:

initial denaturation step at 95° C. for 180 sec;

2-step cycles of 15 sec at 95° C. (1st step) and 15 sec at 62-68.5° C. (2nd step, repeated 40 to 50 times.

4. The method of claim 1, wherein the botanical composition is a plant extract.

5. The method of claim 2, wherein said rt-PCR is conducted under the following conditions:

initial denaturation step at 95° C. for 180 sec;

2-step cycles of 15 sec at 95° C. (1st step) and 15 sec at 62-68.5° C. (2nd step) repeated 40 to 50 times.

6. The method of claim 2, wherein the botanical composition is a plant extract.

7. The method of claim 3, wherein the botanical composition is a plant extract.

8. The method of claim 5, wherein the botanical composition is a plant extract.

* * * * *

SEQUENCE LISTING

<160> NUMBER OF SEQ ID NOS: 14

<210> SEQ ID NO 1
<211> LENGTH: 131
<212> TYPE: DNA
<213> ORGANISM: Unknown
<220> FEATURE:
<223> OTHER INFORMATION: Vaccinium myrtillus

<400> SEQUENCE: 1
gcattgcgtc acccactccc ccgtgcccc aagcgggcac gtcggagcgt gggcggatat      60
tggccccccg ttcgcatccg tgcgcggtcg gcctaaaaaa cgggtcccca atgacggaca     120
tcacgacaag t                                                        131

<210> SEQ ID NO 2

```
<211> LENGTH: 170
<212> TYPE: DNA
<213> ORGANISM: Unknown
<220> FEATURE:
<223> OTHER INFORMATION: Vaccinium myrtillus

<400> SEQUENCE: 2
tgaaggcacg tctgcctggg cgtcacgcat tgcgtcaccc actcccccg tgccccaagc      60 gggcacgtcg gagcgtgggc ggatattggc cccccgttcg catccgtgcg cggtcggcct     120
aaaaaacggg tccccaatga cggacatcac gacaagtggt ggttgctaaa             170

<210> SEQ ID NO 3
<211> LENGTH: 230
<212> TYPE: DNA
<213> ORGANISM: Unknown
<220> FEATURE:
<223> OTHER INFORMATION: Vaccinium myrtillus

<400> SEQUENCE: 3
ttgcagaatc ccgtgaacca tcgagtcttt gaacgcaagt tgcgcctgaa gccattaggt      60
tgaaggcacg tctgcctggg cgtcacgcat tgcgtcaccc actcccccg tgccccaagc     120 gggcacgtcg gagcgtgggc ggatattggc cccccgttcg catccgtgcg cggtcggcct     180
aaaaaacggg tccccaatga cggacatcac gacaagtggt ggttgctaaa             230

<210> SEQ ID NO 4
<211> LENGTH: 275
<212> TYPE: DNA
<213> ORGANISM: Unknown
<220> FEATURE:
<223> OTHER INFORMATION: Vaccinium myrtillus

<400> SEQUENCE: 4
ccatcgagtc tttgaacgca agttgcgcct gaagccatta ggttgaaggc acgtctgcct      60
gggcgtcacg cattgcgtca cccactcccc ccgtgcccca agcggcacg tcggagcgtg     120 ggcggatatt ggcccccccgt tcgcatccgt gcgcggtcgg cctaaaaaac gggtccccaa     180
tgacggacat cacgacaagt ggtggttgct aaaccgtcgc gtcacgtcgt gcatgccatc     240
gtttgttgcg ggttggccca tttgaccctg aagtg                           275

<210> SEQ ID NO 5
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 5
gcattgcgtc acccactc                                              18

<210> SEQ ID NO 6
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 6
acttgtcgtt gaatgtccgt ca                                        22

<210> SEQ ID NO 7
<211> LENGTH: 18
```

```
<212> TYPE: DNA
<213> ORGANISM: Artificial Sequence
<220> FEATURE:
<223> OTHER INFORMATION: oligonucleotide primer

<400> SEQUENCE: 7
tgaaggcacg tctgcctg                                                    18

<210> SEQ ID NO 8
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 8
tttagcaacc accacttgtc gt                                               22

<210> SEQ ID NO 9
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 9
ttgcagaatc ccgtgaacca                                                  20

<210> SEQ ID NO 10
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 10
tttagcaacc accacttgtc gt                                               22

<210> SEQ ID NO 11
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 11
ccatcgagtc tttgaacgca                                                  20

<210> SEQ ID NO 12
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 12
cacttcaggg tcaaatgggc                                                  20

<210> SEQ ID NO 13
<211> LENGTH: 16
<212> TYPE: DNA
<213> ORGANISM: Artificial Sequence
<220> FEATURE:
<223> OTHER INFORMATION: oligonucleotide probe

<400> SEQUENCE: 13
```

-continued

```
acgtcggagc gtgggc                                              16

<210> SEQ ID NO 14
<211> LENGTH: 18
<212> TYPE: DNA
<213> ORGANISM: Artificial Sequence
<220> FEATURE:
<223> OTHER INFORMATION: oligonucleotide probe

<400> SEQUENCE: 14
tagggcgggt aagtgagt                                            18
```